US006288096B1

(12) United States Patent
Andersson et al.

(10) Patent No.: US 6,288,096 B1
(45) Date of Patent: Sep. 11, 2001

(54) THIAZOLIDINEDIONE, OXAZOLIDINEDIONE AND OXADIAZOLIDINEDIONE DERIVATIVES

(75) Inventors: Kjell Andersson; Maria Boije; Eva-Lotte Lindstedt; Bengt Ljung; Bo Nordén, all of Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/091,875

(22) PCT Filed: Jun. 4, 1998

(86) PCT No.: PCT/SE98/01066

§ 371 Date: Jun. 25, 1998

§ 102(e) Date: Jun. 25, 1998

(87) PCT Pub. No.: WO98/57941

PCT Pub. Date: Dec. 23, 1998

(30) Foreign Application Priority Data

Jun. 17, 1997 (SE) .................................... 9702305

(51) Int. Cl.[7] ....................... C07D 277/34; A61K 31/425

(52) U.S. Cl. ................... 514/369; 514/364; 514/376; 548/132; 548/183; 548/226

(58) Field of Search ................... 548/183, 132, 548/226; 514/364, 369, 376

(56) References Cited

U.S. PATENT DOCUMENTS 5,223,522  6/1993  Clark et al. .

FOREIGN PATENT DOCUMENTS 0008203  2/1980  (EP) .
0139421  5/1985  (EP) .

OTHER PUBLICATIONS

Sohda, et al., Chem. Pharm. Bull. 30: 3580–3600 (1982).

*Primary Examiner*—Robert Gerstl
(74) *Attorney, Agent, or Firm*—White & Case LLP

(57) ABSTRACT

Novel thiazolidinedione, oxazolidinedione and oxadiazolidinedione derivatives, process for their manufacture, pharmaceutical preparations containing them and the use of the compounds in conditions associated with insulin resistance.

11 Claims, No Drawings

THIAZOLIDINEDIONE, OXAZOLIDINEDIONE AND OXADIAZOLIDINEDIONE DERIVATIVES

FIELD OF INVENTION

The present invention relates to certain novel thiazolidinedione, oxazolidinedione and oxadiazolidinedione derivatives, to a process for preparing such derivatives, having the utility in clinical conditions associated with insulin resistance, to methods for their therapeutic use and to pharmaceutical compositions containing them.

BACKHROUND OF THE INVENTION

Insulin resistance, defined as reduced sensitivity to the actions of insulin in the whole body or individual tissues such as skeletal muscle, myocardium, fat and liver prevail in many individuals with and without diabetes mellitus. The insulin resistance syndrome, IRS, refers to a cluster of manifestations including insulin resistance with accompanying hyperinsulinemia, possibly non-insulin-dependent diabetes mellitus (NIDDM); arterial hypertension; central (visceral) obesity; dyslipidemia observed as deranged lipoprotein levels typically characterized by elevated VLDL (very low density lipoproteins) and reduced HDL (high density lipoproteins) concentrations; and reduced fibrinolysis.

Recent epidemiological research has documented that individuals with insulin resistance run a greatly increased risk of cardiovascular morbidity and mortality, notably suffering from myocardial infarction and stroke. In non-insulin-dependent diabetes mellitus, these atherosclerosis related conditions cause up to 80% of all deaths.

In clinical medicine there is at present only limited awareness of the need to increase the insulin sensitivity in IRS and thus to correct the dyslipidemia which is considered to cause the accelerated progress of atherosclerosis.

Furthermore there is at present no pharmacotherapy available to adequately correct the metabolic derangements associated with IRS. To date, the treatment of NIDDM has been focused on correction of the deranged control of carbohydrate metabolism associated with the disease. Stimulation of endogenous insulin secretion by means of secretagogues, like sulphonylureas, and if necessary administration of exogenous insulin are methods frequently used to normalize blood sugar but that will, if anything, further enhance insulin resistance and will not correct the other manifestations of IRS nor reduce cardiovascular morbidity and mortality. In addition such treatment involves a significant risk of hypoglycemia with associated complications.

Other therapeutic strategies have focused on aberrations in glucose metabolism or absorption, including biguanides, such as methformin, or glucosidase inhibitors, such as acarbose. Although these agents have been efficacious to a degree, their limited clinical effect is associated with side effects.

A novel therapeutic strategy involves the use of insulin sensitizing agents, such as the thiazolidinediones. Ciglitazone is the prototype in this class. In IRS these compounds seem to correct insulin resistance and the associated hypertrigiyceridaemia and hyperinsulinemia, as well as hyperglycemia in diabetes, by improving insulin sensitivity via an effect on lipid transport and handling, leading to enhanced insulin action in skeletal muscle, liver and adipose tissue.

Ciglitazone as well as later described thiazolidinediones in clinical development either have been discontinued reportedly due to unacceptable toxicity or show inadequate potency. Therefore there is a need for new and better compounds with insulin sensitizing properties.

PRIOR ART

EP 08 203 discloses thiazolidinedione derivatives of the general formula:

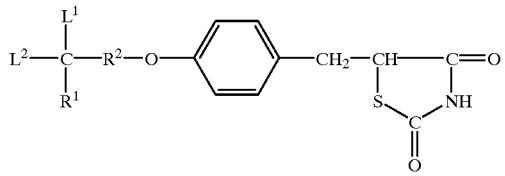

wherein Ris alkyl, cycloalkyl, phenylalkyl, phenyl, a five- or six membered heterocyclic group including one or two hetero-atoms selected from nitrogen, oxygen and sulphur or a group of the formula

(where $R^3$ and $R^4$ are the same or different and each is lower alkyl or $R^3$ and $R^4$ are combined with each other either directly or interrupted by a heteroatom selected from nitrogen, oxygen and sulphur to form a five- or six-membered ring); $R^2$ means a bond or a lower alkylene group; $L^1$ and $L^2$ are the same or different and each is lower alkyl or $L^1$ and $L^2$ are combined to form an alkylene group, provided that, when $R^1$ is other than alky, $L^1$ and $L^2$ may be further hydrogen, as remedies for diabetes and hyperlipemia.

One compound comprised by the formula above is

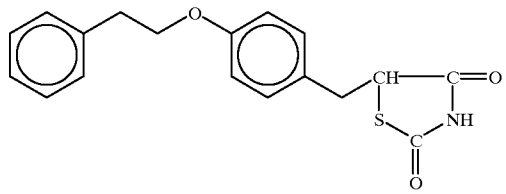

This compound has been reported [Chem. Pharm. Bull. 30(10)3580–3600 (1982)] to have undesirable effects, such as a considerable increase in liver lipids.

EP 139 421 discloses a compound of the formula

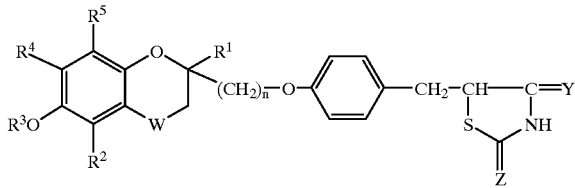

wherein
  $R^1$ and $R^2$ are the same or different and each represents a hydrogen atom or a $C_1$–$C_5$ alkyl group;
  $R^3$ represents a hydrogen atom, a $C_1$–$C_6$ aliphatic acyl group, a ($C_5$–$C_7$ cycloalkane) carbonyl group, an aromatic acyl group which is a benzoyl or naphthoyl group optionally with one or more nitro, amino, alkylamino, dialkylamino, alkoxy, halo, alkyl or hydroxy substituents, a heterocyclic acyl group having one or more oxygen, sulphur or nitrogen hetero atoms and with 4 to 7 ring atoms, an optionally halosubstituted phenylacetyl or phenylpropionyl group, a cinnamoyl group, a ($C_1$–$C_6$ alkoxy) carbonyl group or a benzoyloxycarbonyl group;

$R^4$ and $R^5$ are the same or different and each represents a hydrogen atom, a $C_1$–$C_5$ alkyl group or a $C_1$–$C_5$ alkoxy group, or $R^4$ and $R^5$ together represent a $C_1$–$C_4$ alkylenedioxy group;

n is 1, 2 or 3;

W represents the —CH—, >CO or >CH—$OR^6$ group (in which $R^6$ represents any one of the atoms or groups defined for $R^3$ and may be the same as or different from $R^3$); and Y and Z are the same or different and each represents an oxygen atom or an imino (=NH) group, having the ability to lower blood lipid and blood sugar levels.

Among the compounds comprised by the general formula above is troglitazone having the chemical formula

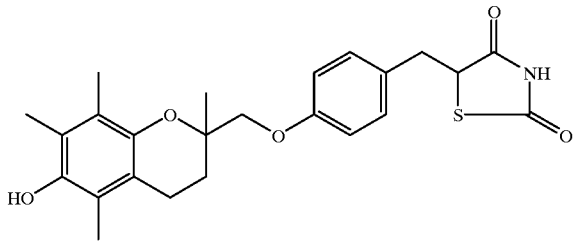

This substance has a very low potency in animal models of IRS.

DESCRIPTION OF THE INVENTION

It has now been found that compounds of the general formula (I)

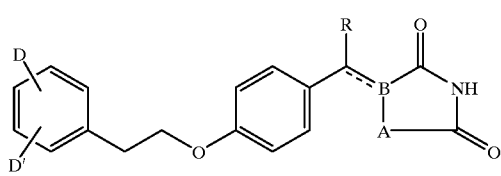

and stereo and optical isomers and racemates thereof as well as pharmaceutically acceptable salts, solvates and hydrates thereof, in which formula === is a single or double bond, R is H or alkyl, A is S, O or NH, B is C, CH or N, D is situated in the ortho, meta or para position and is representing CN or —X—Y—Z, D' is situated in the ortho, meta or para position and is representing H, —O-alkyl, alkyl, halogen or —X—Y—Z, wherein X is O, $NR^1$, $SO_2$ or S and $R^1$ is H or alkyl, Y is $SO_2$, CO, or a chemical bond, Z is alkyl, alkyl substituted by one or more fluoro or chloro atoms, aryl, substituted aryl, alkylaryl, $OR^2$ or $NHR^3$, wherein $R^2$ is alkyl aryl, alkylaryl, substituted aryl or substituted alkyl $R^3$ is H, alkyl, aryl, alkylaryl, substituted aryl or substituted alkyl provided that when X is O or $NR^1$, then Y is either $SO_2$ or CO and Z is, when Y is a) $SO_2$, selected from the group consisting of alkyl, alkyl substituted by one or more fluoro or chloro atoms, aryl, substituted aryl and alkylaryl, when Y is b) CO, selected from the group consisting of $OR^2$ and $NHR^3$ wherein $R^2$ and $R^3$ are as defined above, when X is $SO_2$, then Y is a chemical bond and Z is selected from the group consisting of alkyl, alkyl substituted by one or more fluoro or chloro atoms, aryl, substituted aryl, alkylaryl and $OR^2$, wherein $R^2$ is as defined above, when X is S, then Y is a chemical bond and Z is selected from the group consisting of alkyl, alkyl substituted by one or more fluor or chloro atoms, aryl, substituted aryl and alkylaryl, and further provided that when B is N, A is O, are effective in conditions associated with insulin resistance.

Preferred compounds of the invention are those of the formula I wherein === is a single or double bond, R is a H or alkyl, A is S or O, B is C, CH or N, D is situated in the ortho, meta or para position and is representing —X—Y—Z, D' is situated in the ortho, meta or para position and is representing H, —O-alkyl or —X—Y—Z, X is O, $NR^1$, $SO_2$ or S wherein $R^1$ is H or alkyl, Y is $SO_2$, CO or a chemical bond, Z is alkyl, aryl, alkylaryl, substituted aryl, $CF_3$, $OR^2$, $NHR^3$, wherein $R^2$ and $R^3$, are as defined above, provided that when X is O or $NR^1$, then Y is either $SO_2$ or CO and Z is, when Y is a) $SO_2$, selected from the group consisting of alkyl, $CF_3$, aryl, substituted aryl and alkylaryl, when Y is b) CO, selected from the group consisting of $OR^2$ and $NHR^3$ wherein $R^2$ and $R^3$ are as defined above, when X is $SO_2$, then Y is a chemical bond and Z is selected from the group consisting of alkyl, $CF_3$, aryl, substituted aryl, alkylaryl and $OR^2$, wherein $R^2$ is as defined above, when X is S, then Y is a chemical bond and Z is selected from the group consisting of alkyl, $CF_3$, substituted aryl and alkylaryl, and further provided that when B is N, A is O.

Further preferred compounds of the invention are those of the formula I wherein === is a single or double bond, R is H, A is S, B is C or CH, D is situated in the ortho, meta or para position and is representing —X—Y—Z, D' is H, X is O, $NR^1$, $SO_2$ or S wherein $R^1$ is H or alkyl, Y is $SO_2$, CO or a chemical bond, Z is alkyl, aryl, alkylaryl, substituted aryl, $CF_3$, $OR^2$ or $NHR^3$, wherein $R^2$ and $R^3$ are as defined above, provided that
- when X is O or NR$^1$, then Y is either SO$_2$ or CO and Z is, when Y is a) SO$_2$, selected from the group consisting of alky, CF$_3$, aryl, substituted aryl and alkylaryl, when Y is b) CO, selected from the group consisting of OR$^2$ and NHR$^3$ wherein R$^2$ and R$^3$ are as defined above,
- when X is SO$_2$, then Y is a chemical bond and Z is selected from the group consisting of alkyl, CF$_3$, aryl, substituted aryl, alkylaryl and OR$^2$, wherein R$^2$ is as defined above,
- when X is S, then Y is a chemical bond and Z is selected from the group consisting of alkyl, CF$_3$, aryl, substituted aryl and alkylaryl.

Still further preferred compounds of the invention are those of the formula I wherein ≡≡≡ is a single or double bond,
R is H,
A is S,
B is C or CH,
D is situated in the ortho, meta or para position and is representing —X—Y—Z,
D' is H,
X is O, NH, SO$_2$ or S,
Y is SO$_2$, CO or a chemical bond,
Z is alkyl, aryl, alkylaryl, substituted aryl, CF$_3$, OR$^2$ or NHR$^3$, wherein R$^2$ and R$^3$ are as defined above,
provided that
- when X is O or NH, then Y is either SO$_2$ or CO and Z is, when Y is a) SO$_2$, selected from the group consisting of alkyl, CF$_3$, aryl, substituted aryl and alkylaryl, when Y is b) CO, selected from the group consisting of OR$^2$ and NHR$^3$ wherein R$^2$ and R$^3$ are as defined above,
- when X is SO$_2$, then Y is a chemical bond and Z is selected from the group consisting of alkyl, CF$_3$, aryl, substituted aryl, alkylaryl and OR$^2$, wherein R$^2$ is as defined above,
- when X is S, then Y is a chemical bond and Z is selected from the group consisting of alkyl, CF$_3$, aryl, substituted aryl and alkylaryl.

Still further preferred compounds of the invention are those in the formula I wherein D is situated in the para position.

Still further preferred compounds of the invention are those of the formula I wherein ≡≡≡ is a single bond,
R is H,
A is S,
B is CH,
D is situated in the para position and is representing —X—Y—Z,
D' is H,
X is O or NH
Y is SO$_2$ or CO,
Z is alkyl, aryl alkylaryl, substituted aryl, CF$_3$, OR$^2$ and NHR$^3$, wherein R$^2$ and R$^3$, are as defined above,
provided that
- when X is O or NH, then Y is either SO$_2$ or CO and Z is, when Y is a) SO$_2$, selected from the group consisting of alkyl, CF$_3$, aryl, substituted aryl and alkylaryl, when Y is b) CO, selected from the group consisting of OR$^2$ and NHR$^3$ wherein R$^2$ and R$^3$ are as defined above.

Still further preferred compounds of the invention are those of the formula I wherein ≡≡≡ is a single bond,
R is H,
A is S,
B is CH,
D is situated in the para position and is representing —X—Y—Z,
D' is H,
X is O or NH
Y is SO$_2$ or CO,
Z is alkyl, NHR$^3$ or OR$^2$, wherein R$^2$ is alkyl and R$^3$ is alkyl,
provided that
- when X is O or NH, then Y is either SO$_2$ or CO and Z is, when Y is a) SO$_2$, selected from the group consisting of alkyl, when Y is b) CO, selected from the group consisting of OR$^2$ and NHR$^3$ wherein R$^2$ and R$^3$ are as defined above.

Still further preferred compounds of the invention are those having the chemical formulas

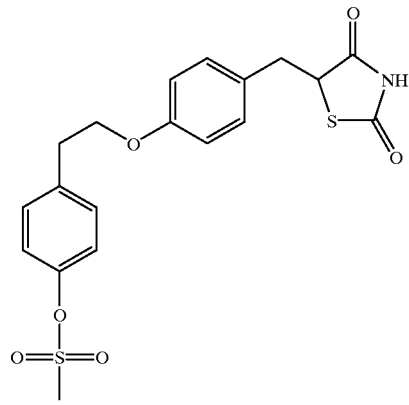

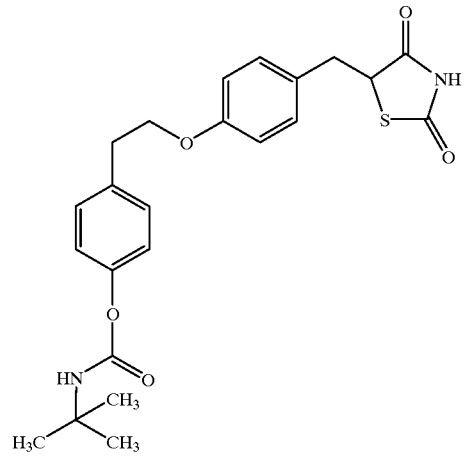

or

-continued

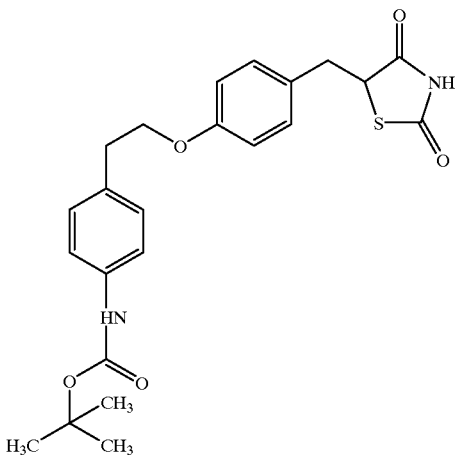

In the present specification the expression "pharmaceutically acceptable salts" is intended to define but is not limited to such base salts as the alkali metal salts (e.g. sodium, lithium and potassium), alkaline earth metal salts (e.g. calcium, barium and magnesium), aluminum, zinc and bismuth salts, ammonium salts, salts with basic amino acids, such as arginine, lysine, and salts with organic amines such as ethanolamine, ethylenediamine, triethanoleamine, benzylphenethylamine, diethylamine, tromethamine, benzathine, chloroprocaine, choline, meglumine, procaine, clemizole and piperazine.

Throughout the specification and the appended claims, a given chemical formula or name shall encompass all stereo and optical isomers and racemates thereof where such isomers exist, as well as pharmaceutically acceptable salts thereof and solvates thereof such as for instance hydrates.

The following definitions shall apply throughout the specification and the appended claims.

Unless otherwise stated or indicated, the term "alkyl" denotes a straight or branched alkyl group having from 1 to 6 atoms. Examples of said alkyl include methyl, ethyl, n-propyl, isopropyl, n-butyl, iso-butyl, sec-butyl, t-butyl and straight- and branched-chain pentyl and hexyl.

Unless otherwise stated or indicated, the term "halogen" shall mean fluorine, chlorine, bromine or iodine.

Unless otherwise stated or indicated, the term "aryl" denotes a phenyl, furyl, thienyl or pyridyl group.

Unless otherwise stated or indicated, the term "substituted aryl" denotes an aryl group as defined above which is substituted by one or more alkyl, alkoxy, halogen, amino or nitro groups.

Unless otherwise stated or indicated, the term "substituted alkyl" denotes an alkyl group as defined above which is substituted by one or more alkyl, alkoxy, halogen, amino or nitro groups.

Unless otherwise stated or indicated, the term "alkylaryl" denotes a

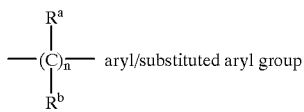

wherein n is an integer 1 to 6 and $R^a$ and $R^b$ are the same or different and each represents a substituted or unsubstituted alkyl or aryl group as defined above.

METHODS OF PREPARATION

The compounds of the invention may be prepared as outlined below according to any of methods A–C. However, the invention is not limited to these methods, and the compounds may also be prepared as described for structurally related compounds in the prior art.

A. The compounds of the invention of formula I wherein A is S or O, B is C or CH can be prepared by a condensation reaction of a carbonyl compound of the formula II

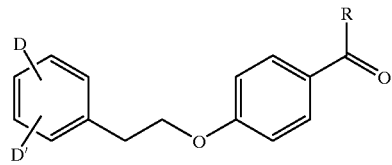

with a compound of the formula

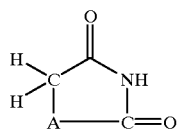

and if desired, followed by reduction of the obtained compound.

The compound of the formula II is prepared by coupling a compound of formula

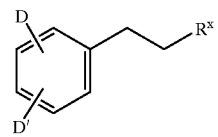

with a compound of formula

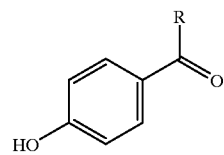

at, for example alkylation conditions or by a Mitzunobu reaction (Tsunoda, Tetr. Lett. 34, 1639–42 (1993), when necessary followed by modifications of the D-group as described in the experimental section.

The group $R^x$ can be a sulfonate, a halogen or an alcohol.

The compound of formula

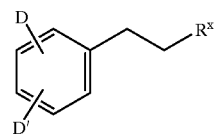

can be prepared by standard procedures known to anyone skilled in the art, from commercially available starting materials.

In the condensation step, an approximately equimolar amounts of reactants are heated in the presence of a mild base, such as sodium acetate or piperidine acetate, to provide the olefin compound of formula I wherein ═══ is a double bond. This step may be carried out in the presence of a reaction inert solvent or in the absence of solvent at a temperature which is sufficiently high to cause at least partial melting of the reaction mixture. A preferred such temperature is in the range of 100° C. to 250° C.

In a typical such reaction the aldehyde or ketone starting material and thiazolidinedione/oxazolidinedione are combined in approximately equimolar amounts with a molar excess, ref. 1–4 fold molar excess, of anhydrous sodium acetate and the mixture is heated, at a temperature high enough to effect melting and if necessary under vacuum. The olefin (compound of formula I wherein ≡≡≡ is a double bond) can then be isolated by mixing with water or acetone and followed by filtration of the precipitate, to obtain the crude product which is purified if desired, e.g. by recrystallization or by standard chromatographic methods.

This reaction also takes place conveniently in a solvent such as toluene in presence of piperidine acetate. The resulting solution is refluxed with water separation in a Dean-Stark apparatus. The solution is then cooled and the olefin product isolated and purified by standard methods.

The reduction of the olefin may be carried out by employing a wide variety of reducing agents which are known to reduce carbon-carbon double bonds, such as catalytic hydrogenation in the presence of an appropriate catalyst, magnesium or sodium amalgam in a lower alcohol such as methanol, or hydrogen transfer reagents such as diethyl-2,5-dimethyl-1,4-dihydropyridine-3,5-dicarboxylate.

The catalytic hydrogenation can be conducted in alcohol, cellosolves, protic polar organic solvents, ethers, alkoxyalkanes, lower aliphatic acids, and particularly methanol, ethanol, methoxyethanol, dimethylformamide, tetrahydrofaran, dioxane, dimethoxyethane, ethyl acetate or acetic acid is preferably used alone or as mixtures. Examples of the catalyst used include palladium black, palladium on carbon and platinum oxide. This reaction can proceed at normal temperature under normal pressure or at elevated temperature under increased pressure depending on the reactivity of the aimed reaction.

In case of hydrogen transfer reaction with diethyl-2,5-dimethyl-1,4-dihydropyridine-3,5-dicarboxylate, the reaction is conducted by mixing equimolar amounts of reactants and warming the mixture to melting (140–250° C.) under inert atmosphere or under vacuum.

B. The compounds of the invention of formula I can be prepared by reaction of a compound of the formula

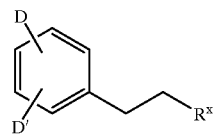

III with a compound of the formula

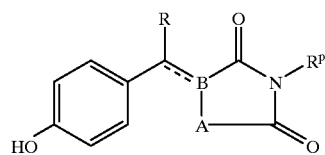

IV wherein D, D', R', A and B are as defined above, $R^x$ is a leaving group or an —OH group and $R^p$ is hydrogen or a protecting group, either by an alkylation reaction or a Mitzunobu reaction, when necessary followed by deprotection of the protective group $R^p$.

In an alkylation reaction the leaving group $R^x$ can be a sulfonate such as mesylate, nosylate, tosylate, or a halogen, such as bromine or iodine. The compounds of formula III and IV in approximately equimolar amounts or with an excess of either compound are heated to reflux temperature in an inert solvent, such as isopropanol or acetonitrile, in the presence of a base, such as potassium carbonate or cesium carbonate.

The mixture is refluxed for the necessary time, typically between 0.5 h to 24 h. The work up procedure usually includes filtration, for removal of solid salt, evaporation and extraction with water and an organic solvent such as dichloromethane, ethylacetate, or diethyl ether. The crude product is purified if desired e.g. by recrystallization or by standard chromatographic methods.

The Mitzunobu reaction can be carried out according to standard methods.

In a typical Mitzunobu reaction a compound of formula III, wherein the group $R^x$ is a hydroxyl group, and a compound of formula IV are mixed in an inert solvent, such as chloroform or dichloromethane, in approximately equimolar amounts. A slight molar excess, 1–4 eqvivalents, of azodicarboxylate, such as DEAD (diethyl azodicarboxylate) or ADDP (azodicarbonyl dipiperidine) and a phosphine (1–4 equivalents), such as tributylphosphine or triphenylphosphine are added and the reaction is stirred at a temperature high enough—for example room temperature—and a time long enough (1–24 hours) to obtain the crude product, which can be worked up with standard literature methods and if desired purified, e.g. by standard chromatographic methods.

C. The compounds of the invention of the formula I wherein A is O, B is N, and ≡≡≡ is a single bond can be prepared by reaction of a compound of the formula

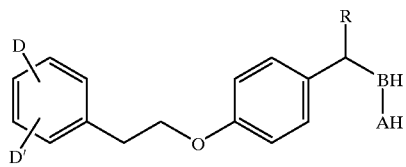

V with a compound of the formula VI

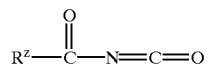

VI wherein D, D', R, A and B are as defined above and $R^z$ is a halogen, preferably chlorine.

In a typical reaction, the compound of formula VI is added to a cool solution of a compound of formula V in an inert solvent, such as tetrahydrofuran or diethylether, preferentially at a slow enough speed to keep the temperature below −5° C. The reaction mixture is stirred at a temperature between −10° C. and room temperature for an appropriate time.

The reaction can be worked up by acidification, e.g. by pouring it onto a water solution of hydrochloric acid, and extraction with the aid of an organic solvent. The crude product of the desired compound can be purified if desired by crystallization or standard chromatographic methods.

The compounds of formula V can be prepared by reduction of a compound of formula VII

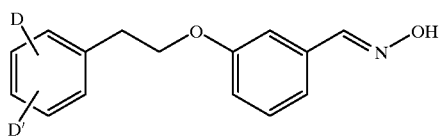

in a solvent such as tetrahydofuran and/or methanol, using an excess of a reducing agent, such as sodium cyanoborohydride.

In a typical such reaction, an excess of the reducing agent, e.g. sodium cyanoborohydride, is added to a solution of a compound of formula VII in methanol and tetrahydrofuran.

Hydrochloric acid in a solvent, such as dioxane can be added.

The reaction can be worked up according to literature and if necessary purified by standard chromatographic methods to give the compound of formula V.

The compound of formula VII can be prepared by reacting a compound of formula II with hydroxyl amine.

A typical such reaction is performed by adding an excess of hydroxyl amine hydrochloride and a base, such as sodium acetate in water, to a solution of a compound of formula II in a solvent, such as ethanol. The reaction can be performed at a temperature of 50° C. for 1.5 hours.

The crude product can be purified by crystallization to give the compound of formula VII.

The compound of formula II can be prepared as described in method A.

Pharmaceutical Preparations

The compounds of the invention will normally be administered via the oral, parenteral, buccal, rectal, vaginal, transdermal and/or nasal route and/or via inhalation, in the form of pharmaceutical preparations comprising the active ingredient either as a free acid, or a pharmaceutically acceptable organic or inorganic base addition salt, in a pharmaceutically acceptable dosage form. Depending upon the disorder and patient to be treated and the route of administration, the compositions may be administered at varying doses.

The compounds of the invention may also be combined with other therapeutic agents which are useful in the treatment of disorders associated with the development and progress of atherosclerosis such as hypertension, hyperlipidemias, dyslipidemias, diabetes and obesity.

Suitable daily doses of the compounds of the invention in the therapeutic treatment of humans are about 0.01–10 mg/kg body weight.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) are readily adapted to clinical use for treatment of clinical conditions associated with reduced sensitivity to insulin (insulin resistance) and other metabolic disorders. These clinical conditions will include but will not be limited to abdominal obesity, arterial hypertension, hyperinsulinemia, hyperglycemia, dyslipidemia, particularly elevated triglycerides and nonesterified fatty acids in blood associated with elevated VLDL and reduced HDL lipoproteins. Treatment with the present compounds is expected to lead to lower cardiovascular morbidity and mortality i.e. reduced incidence of ischemic heart disease including myocardial infarction, cerebrovascular disease including stroke as well as peripheral atherosclerotic disease including renal disease and peripheral arterial insufficiency of the extremities.

WORKING EXAMPLES

Example 1

4-Cyanophenethyl methanesulfonate 3.7 g (25 mmole) p-cyanophenethylalcohol was dissolved in 15 ml dichloromethane, 5.2 ml (87.5 mmole) triethylamine was added and the mixture was cooled on an ice bath. 2.52 ml (32.5 mmole) methanesulfonyl chloride in 5 ml dichloromethane was slowly added at 0–7° C. The reaction was allowed to reach room temperature and then stirred at room temperature. The reaction mixture was washed with cooled 2 N hydrochloric acid, water, dried (sodium sulfate), filtered and the solvent was evaporated in vacuo to give 5.3 g (yield 95%) of 4-cyanophenethyl methanesulfonate.

4-[2-(4-Formylphenoxy)ethyl]benzonitrile 8.55 g (38 mmole) 4-cyanophenethyl methanesulfonate, 4.64 g (38 mmole) p-hydroxybenzaldehyde and 18.7 g (57 mmole) cesium carbonate in 150 ml acetonitrile was refluxed over night. The salt was filtered off and the solvent evaporated in vacuo. The residue was treated with 2 M sodium hydroxide and dichloromethane. The organic phase was dried and evaporated in vacuo. Purification by chromatography on silica gel using dichloromethane as eluent gave 1.6 g (yield 17%) of 4-[2-(4-formylphenoxy)ethyl] benzonitrile.

5-(4-[2-(4-Cyanophenyl)ethoxy]benzylidene)thiazolidine-2,4-dione 2.4 g (9.6 mmole) 4-[2-(4-formylphenoxy)ethyl] benzonitrile, 1.4 g (12 mmole) 2,4-thiazolidinedione and 1.96 g (24 mmole) sodium acetate was mixed and heated under vacuum to 140° C. The reaction mixture melted and was after 30 minutes removed from the heat. Water:acetone (2:1) was added and filtration followed by recrystallization in trifluoroacetic acid/acetic acid gave 1.79 g (yield 52%) of 5-(4-[2-(4-cyanophenyl)ethoxy]benzylidene)thiazolidine-2,4-dione.

$^1$H-NMR (300 MHz; DMSO-$d_6$): δ 3.05–3.2 (tr, 2H), 4.22–4.36 (tr, 2H), 7.0–7.12 (d, 2H), 7.45–7.58 (m, 4H), 7.72 (s, 1H), 7.72–7.82 (m, 2H). $^{13}$C-NMR (75 MHz; DMSO-$d_6$): δ 35.0, 67.9, 109.5, 115.6, 119.2, 120.7, 125.9, 130.4, 132.0, 132.4, 132.5, 144.7, 160.3, 167.8, 168.3.

5-([4-[2-(4-Cyanophenyl)ethoxy]phenyl]methyl)thiazolidine-2,4-dione 3.9 g (11 mmole) 5-(4-[2-(4-cyanophenyl)ethoxy] benzylidene)thiazolidine-2,4-dione and 3.88 g (15 mmole) diethyl-1,4-dihydro-2,6-dimethyl-3,5-pyridine dicarboxylate were mixed and heated to 210° C. under vacuum for 1 hour. The solid material was dissolved in ethyl acetate, evaporated in vacuo, purified by chromatography on silica gel with first dichloromethane, then dichloromethane:diethyl ether (95:5) and finally dichloromethane:methanol (95:5) as eluents. Crystallization in acetone/water gave 0.65 g (yield 17%) of the desired product.

$^1$H-NMR (300 MHz; DMSO-$d_6$): δ 2.98–3.21 (m, 3H), 3.21–3.34 (dd, 1H), 4.16–4.24 (tr, 2H), 4.82–4.89 (dd, 1H), 6.22–6.90 (m, 2H), 7.09–7.17 (m, 2H), 7.49–7.58 (m, 2H), 7.74–7.82 (m, 2H).

Example 2

5-([4-Benzyloxyphenyl]methyl)oxazolidine-2,4-dione 5.5 g (19.2 mmole) 2-hydroxy methyl 3-(4-benzyloxyphenyl)propionate, 1.98 g urea, 1.38 g sodium methoxide, 4.9 ml methanol and 49 ml ethanol was stirred for 2 hours at room temperature, then refluxed over night. The reaction mixture was poured on to 305 ml 2 N hydrochloric acid. The product was extracted with ethyl acetate, washed with aqueous sodium bicarbonate, dried and the solvent was evaporated in vacuo. The crude product was purified by chromatography on silica gel using dichloromethane:methanol (95:5) as eluent to give 2.75 g (yield 48%) of 5-([4-benzyloxyphenyl]methyl)oxazolidine-2,4-dione.

5-([4-Hydroxyphenyl]methyl)oxazolidine-2,4-dione 2.75 g (9.25 mmole) 5-([4-benzyloxyphenyl]methyl) oxazolidine-2,4-dione was hydrogenated at 50 psi over night in 1,4-dioxan using Pd/C as catalyst to give 1.8 g (yield 94%) of 5-([4-hydroxyphenyl]methyl)oxazolidine-2,4-dione.

3-Triphenylmethyl-5-([4-hydroxyphenyl]methyl) oxazolidine-2,4-dione 0.33 g (1.18 mmole) triphenylmethyl chloride was added to a solution of 0.245 g (1.18 mmole) 5-([4-hydroxyphenyl] methyl)oxazolidine-2,4-dione, 0.165 ml (1.18 mmole) triethylamine, 5 ml dichloromethane and 5 ml dimethylformamide on an icebath. The temperature of the reaction mixture was allowed to reach room temperature. After 1.5 hours 0.05 ml more triethylamine was added. After 2 hours ethyl acetate and water were added and the phases were seperated. The organic phase was dried (sodium sulfate), the solvent was evaporated and the crude product was purified by chromatography on silica gel using heptane:ethyl acetate (3:2) as eluent to give 0.32 g (yield 60%) 3-triphenylmethyl-5-([4-hydroxyphenyl]methyl)oxazolidine-2,4-dione.

3-Triphenylmethyl-5-([4-[2-(4-methanesulfonyloxyphenyl)ethoxy]phenyl]methyl) oxazolidine-2,4-dione 0.28 g (0.623 mmole) 3-triphenylmethyl-5-([4-hydroxyphenyl]methyl)oxazolidine-2,4-dione was under argon atmosphere added to a cooled solution of 0.148 g (0.685 mmole) 2-[4-(methylsulfonyloxy)phenyl]-1-ethanol, 0.173 g (0.685 mmole) 1,1'-(azodicarbonyl)-dipiperidine and 0.18 g (0.685 mmole) triphenylphosphine in 6 ml dichloromethane. After stirring for 3 hours the reaction mixture was filtered and the crude product was purified by chromatography on silica gel using heptane:ethyl acetate (2:2) as eluent to give 0.215 g (yield 53%) of 3-triphenylmethyl-5-([4-[2-(4-methanesulfonyloxyphenyl) ethoxy]phenyl]methyl)oxazolidine-2,4-dione.

5-([4-[2-(4-Methanesulfonyloxyphenyl)ethoxy] phenyl]methyl)oxazolidine-2,4-dione 1 ml trifluoroacetic acid was added to a solution of 0.214 g (0.33 mmole) 3-triphenylmethyl-5-([4-[2-(4-methanesulfonyloxyphenyl)ethoxy]phenyl]methyl) oxazolidine-2,4-dione in 10 ml dichloromethane. After stirring for 45 minutes at room temperature 20 ml more of dichloromethane was added, the reaction mixture was washed twice with water, dried (sodium sulfate) and the solvent was evaporated in vacuo. The crude product was purified by chromatography on silica gel using heptane:ethyl acetate:acetic acid (10:10:1) as eluent to give 0.118 g (yield 88%) of 5-([4-[2-(4-methanesulfonyloxyphenyl)ethoxy] phenyl]methyl)oxazolidine-2,4-dione.

$^{13}$C-NMR (75 MHz; CD$_3$OD): δ 36.0, 36.4, 37.4, 69.4, 82.6, 115.6, 123.2, 127.4, 131.7, 132.0, 139.6, 149.6, 157.5, 159.6, 176.0.

Example 3

2-[2,4-Di(benzyloxy)phenyl]-1-ethanol 10 ml (20 mmole) 2 M borane dimethyl sulfide complex in diethyl ether was slowly added to 6.3 g (18.1 mmole) 2,4-dibenzyloxyphenyl acetic acid dissolved in 50 ml dry tetrahydrofuran cooled on an ice bath under nitrogen and then stirred for 7 days at room temperature. The reaction was quenched with water and extracted with ethyl acetate, dried with magnesium sulfate and evaporated. The crude product was purified by chromatography on silica gel using dichloromethane/methanol as eluent to give 2.63 g of the desired product and a mixture of 2,4-dibenzyloxyphenyl acetic acid and the desired product. The mixture was dissolved in 100 ml ethyl acetate, 0.152 g (4 mmole) lithium aluminum hydride was added in portions and the mixture was stirred at room temperature for 6 hours. After 4 hours some more lithium aluminum hydride was added. The reaction was quenched with 1% hydrochloric acid and the solution was filtered. The filtrate was dried with magnesium sulfate and evaporated in vacuo to give 1.3 g more of 2-[2,4-di(benzyloxy)phenyl]-1-ethanol (total yield 3.9 g, 64.4%).

2-(2,4-Dihydroxyphenyl)-1-ethanol 3.7 g (11.1 mmole) 2-[2,4-di(benzyloxy)phenyl]-1-ethanol was hydrogenated in 100 ml ethyl acetate using Pd/C (10%) as catalyst. The reaction mixture was filtered and the filtrate was evaporated in vacuo to give 1.7 g (yield 99%) of 2-(2,4-dihydroxyphenyl)-1-ethanol.

2,4-(Dimethylsulfonyloxy)phenethyl methanesulfonate 5.8 ml (41.5 mmole) triethylamine was added to a mixture of 1.7 g (11 mmole) 2-(2,4-dihydroxyphenyl)-1-ethanol in 100 ml dichloromethane. The mixture was cooled on an icebath and 3 ml (38.6 mmole) methanesulfonyl chloride was added slowly. The reaction mixture was stirred at room temperature for 5 h. As the reaction was not completed, 0.5 ml methanesulfonyl chloride was added and the mixture was stirred at room temperature over night but this gave no better result. The solvent was removed by evaporation in vacuo and 100 ml tetrahydrofuran, 2 ml triethylamine and 1 ml methanesulfonyl chloride were added and the mixture was stirred in room temperature for 1 hour. The solvent was removed by evaporation in vacuo, dichloromethane was added and the solution was washed with water, dilute sodium bicarbonate and brine and dried with magnesium sulfate. The solvent was evaporated in vacuo over night to give 4.4 g of an oil which was directly used in the next step.

4-[2-(4-Formylphenoxy)ethyl]-3-(methylsulfonyloxy)phenyl methanesulfonate 4.4 g (11 mmole) 2,4-di(methylsulfonyloxy)phenethyl methanesulfonate, 2.7 g (22.1 mmole) p-hydroxybenzaldehyde and 3.1 g (22.5 mmole) potassium carbonate in 150 ml acetonitrile was refluxed over night. The solvent was evaporated in vacuo. To the residue was added dichloromethane and water and the phases were separated. The organic phase was washed with water, dried with magnesium sulfate and the solvents were evaporated in vacuo. The residue was purified by chromatography on silica gel twice, using first dichloromethane/methanol and then ethyl acetate/hexane as eluents, to give 0.38 g of 4-[2-(4-formnylphenoxy)ethyl]-3-(methylsulfonyloxy)phenyl methanesulfonate. One of the isolated byproducts was mesylated and worked up as above to give 0.55 g more of the product (yield in 2 steps=20.4%).

5-(4-[2-(2,4-Dimethanesulfonyloxyphenyl)ethoxy] benzylidene)thiazolidine-2,4-dione 0.887 g (2.14 mmole) 4-[2-(4-formylphenoxy)ethyl]-3-(methylsulfonyloxy)phenyl methanesulfonate was dissolved in 8 ml dichloromethane. 0.314 g (2.68 mmole) 2,4-thiazolidinedione and 0.439 g (5.35 mmole) sodium acetate were added and everything was mixed together. The solvent was evaporated in vacuo and the mixture was heated under vacuum to 175° C. and kept at this temperature for 20 minutes (the mixture melted at ca. 100° C.). After cooling the reaction mixture was stirred in water and acetone. Acetic acid was added and the precipitate was collected by filtration, washed with acetone/water, pure water and dried to give 0.76 g (yield 69%) of 5-(4-[2-(2,4-dimethanesulfonyloxyphenyl)ethoxy]benzylidene) thiazolidine-2,4-dione.

$^1$H-NMR (300 MHz; DMSO-$d_6$): δ 3.1–3.23 (tr, 2H), 3.42 (s, 3H), 3.53 (s, 3H), 4.24–4.36 (tr, 2H), 7.06–7.15 (m, 2H), 7.3–7.39 (m, 1H), 7.42–7.48 (m, 1H), 7.5–7.59 (m, 2H), 7.61–7.69 (m, 1H), 7.75 (s, 1H).

5-([4-[2-(2,4-Dimethanesulfonyloxyphenyl)ethoxy] phenyl]methyl)thiazolidine-2,4-dione 0.718 g (1.4 mmole) 5-(4-[2-(2,4-dimethanesulfonyloxyphenyl)ethoxy]benzylidene) thiazolidine-2,4-dione was hydrogenated over night in 100 ml ethyl acetate and 1 ml acetic acid with 1.4 g Pd/C (10%) as catalyst. The catalyst was filtered off and the filtrate was washed with water, dried with magnesium sulfate and evaporated in vacuo to give 0.55 g (yield 76%) of the desired product.

$^1$H-NMR (300 MHz; CDCl$_3$): δ 3.0–3.22 (m, 3H), 3.10 (s, 3H), 3.18 (s, 3H), 3.3–3.5 (dd, 1H), 4.1–4.25 (tr, 2H), 4.4–4.55 (dd, 1H), 6.75–6.9 (m, 2H), 7.05–7.17 (m, 2H), 7.17–7.27 (m, 1H), 7.33 (s, 1H), 7.41–7.52 (m, 2H), 8,5 (bs, 1H). $^{13}$C-NMR (75 MHz; CDCl$_3$): δ 29.6, 37.59, 37.64, 38.5, 53.6, 66.8, 114.8, 116.7, 121.1, 128.0, 130.5, 131.2, 132,4, 147.5, 147.7, 157.9, 170.4, 174.1.

Example 4

4-(4-Methoxyphenylsulfonyloxy)phenethyl 4-methoxy-1-benzenesulfonate 2.76 g (20 mmole) p-hydroxyphenethyl alcohol was dissolved in 80 ml dichloromethane. 6 g triethylamine, 8.5 g (41 mmole) 4-methoxybenzenesulfonyl chloride and 0.2 g 4-dimethyl-aminopyridine were added. The mixture was stirred over night at room temperature and filtered through silica gel with dichloromethane as eluent to give 8.5 g (yield 89%) of 4-(4-methoxyphenylsulfonyloxy)phenethyl 4-methoxy-1-benzenesulfonate.

4-[2-(4-Formylphenoxy)ethyl]phenyl 4-methoxy-1-benzenesulfonate

A mixture of 8.5 g (17.8 mmole) 4-(4-methoxyphenylsulfonyloxy)phenethyl 4-methoxy-1-benzenesulfonate, 2.16 g (17.7 mmole) 4-hydroxybenzaldehyde and 10 g (72.5 mmole) potassium carbonate in 60 g acetonitrile was refluxed over night. The salt was filtered off and the solvent was evaporated. The crude product was purified on silica gel using dichloromethane as eluent to give 7.4 g of 4-[2-(4-formylphenoxy) ethyl]phenyl 4-methoxy-1-benzenesulfonate (slightly polluted with the corresponding styrene product).

5-(4-[2-(4-(4-Methoxyphenylsulfonyloxy)phenyl) ethoxy]benzylidene)thiazolidine-2,4-dione A mixture of 2 g (4.85 mmole) 4-[2-(4-formylphenoxy) ethyl]phenyl 4-methoxy-1-benzenesulfonate and 0.8 g (6.8 mmole) 2,4-thiazolidinedione, 0.4 g piperidine, 0.3 g acetic acid and 20 ml toluene was refluxed with water separation in a Dean-Stark apparatus for 2.5 hours. The solvent was evaporated in vacuo, the residue was dissolved in dichloromethane and washed with potassium hydrogensulfate solution and with water, dried with magnesium sulfate, filtered and the solvent was concentrated in vacuo. 1.2 g of crystals were filtered off and the mother liquid was purified by chromatography on silica gel using dichloromethane/diethylether (gradient) as eluent to give 0.5 g more, totally 1.7 g (yield 69%) of 5-(4-[2-(4-(4-methoxyphenylsulfonyloxy)phenyl)ethoxy]benzylidene) thiazolidine-2,4-dione.

$^1$H-NMR (300 MHz; DMSO-$d_6$): δ 2.9–3.1 (tr, 2H), 3.84 (s, 3H), 4.1–4.3 (tr, 2H), 6.8–7.0 (m, 2H), 7.0–7.2 (m, 2H), 7.2–7.37 (m, 2H), 7.37–7.6 (m, 2H), 7.6–7.85 (m, 3H).

5-([4-[2-(4-(4-Methoxyphenylsulfonyloxy)phenyl) ethoxy]phenyl]methyl)thiazolidine-2,4-dione 1.2 g (2.35 mmole) 5-(4-[2-(4-(4-methoxyphenylsulfonyloxy)phenyl)ethoxy]benzylidene) thiazolidine-2,4-dione was mixed with 200 ml warm ethyl acetate, 2 ml acetic acid and 1.2 g Pd/C (5%, 50% water) and hydrogenated for 4 hours at room temperature. 1.2 g more of the catalyst was added after 2 hours. The catalyst was filtered off and the solvent was evaporated in vacuo. The crude product was purified by chromatography on silica gel using dichloromethane/diisopropyl ether (gradient) as eluent to give 0.5 g of the desired product.

$^1$H-NMR (400 MHz; CDCl$_3$): δ 3.02–3.14 (m, 3H), 3.40–3.48 (dd, 1H), 3.89 (s, 3H), 4.09–4.15 (tr, 2H), 4.47–4.53 (dd, 1H), 6.79–6.85 (m, 2H), 6.90–7.0 (m, 4H), 7.1–7.16 (M, 2H), 7.17–7.23 (m, 2H), 7.73–7.78 (m, 2H). $^{13}$C-NMR (75 MHz; CDCl$_3$): δ 35.0, 37.7, 53.6, 55.7, 68.2, 114.3, 114.8, 122,4, 126.7, 127.8, 130.1, 130.3, 130.7, 137.3, 148.2, 158.1, 164.0, 170.5, 174.3.

Example 5

4-(Methylsulfonyloxy)phenethyl methanesulfonate 27.3 g (0.27 mmole) triethylamine and a solution of 27.2 g (0.239 g mmole) methane sulfonyl chloride in dichloromethane were added to a solution of 15 g (0.108 mmole) p-hydroxyphenethyl alcohol in dichloromethane at 0° C. The reaction was allowed to reach room temperature, then stirred at room temperature and followed by TLC. The reaction mixture was filtered and the filtrate was washed with water. The solution was dried with sodium sulfate and then evaporated in vacuo to give 28 g (yield 88%) of 4-(methylsulfonyloxy)phenethyl methanesulfonate.

4-[2-(4-Formylphenoxy)ethyl]phenyl methanesulfonate 30 g (0.102 mole) 4-(methylsulfonyloxy)phenethyl methanesulfonate was dissolved in acetonitrile and slowly added to a mixture of 31.1 g (0.255 mole) p-hydroxybenzaldehyde and 41.46 g (0.3 mole) potassium carbonate in acetonitrile and refluxed until the starting material was consumed. The salt was filtered off, the solvent evaporated in vacuo, dichloromethane was added and the organic phase was washed with water. After evaporation of the solvent, purification by chromatography on silica gel using dichloromethane as eluent gave 21.6 g (yield 66%) of 4-[2-(4-formylphenoxy)ethyl]phenyl methanesulfonate.

5-(4-[2-(4-Methanesulfonyloxyphenyl)ethoxy]benzylidene)thiazolidine-2,4-dione 1.5 g (4.7 mmole) 4-[2-(4-formylphenoxy)ethyl]phenyl methanesulfonate, 0.68 g (5.8 mmole) 2,4-thiazolidinedione and 0.96 g (11.8 mmole) sodium acetate were mixed and heated under vacuum to 155° C. The reaction mixture melted and was removed from the heat after 15 minutes. Water/acetone (2:1) was added and the mixture was stirred for 1 h. Filtration gave 1.67 g (yield 83%) of 5-(4-[2-(4-methanesulfonyloxyphenyl)-ethoxy]benzylidene)thiazolidine-2,4-dione as yellow crystals.

$^1$H-NMR (400 MHz; DMSO-d$_6$): δ 3.02–3.09 (tr, 2H), 3.32 (s, 3H), 4.22–4.28 (tr, 2H), 7.03–7.09 (m, 2H), 7.24–7.29 (m, 2H), 7.38–7.44 (m, 2H), 7.47–7.52 (m, 2H), 7–68 (s, 1H). $^{13}$C-NMR (75 MHz; DMSO-d$_6$): δ 33.9, 37.2, 68.0, 115.3, 120.2, 122.0, 125.5, 130.5, 131.7, 132.0, 137.4, 147.6, 160.6, 167.3, 167.8.

5-([4-[2-(4-Methanesulfonyloxyphenyl)ethoxy]phenyl]methyl)thiazolidine-2,4-dione 98 g (0.23 mole) 5-(4-[2-(4-methanesulfonyloxyphenyl)ethoxy]benzylidene)thiazolidine-2,4-dione and 89 g (0.35 mole) diethyl-1,4-dihydro-2,6-dimethyl-3,5-pyridine dicarboxylate was heated under reduced pressure until it melted (160° C.). The reaction mixture was allowed to stay at this temperature for 5 hours. The reaction mixture was then taken off the heat and toluene was added when the temperature was below 100° C. The crystals were collected and washed with diethyl ether and recrystallized in toluene to give 77 g (yield 79%) of the desired product.

$^1$H-NMR (600 MHz; CDCl$_3$): δ 3,05–3,105 (m, 3H), 3.12 (s, 3H), 3,38–3,45 (m, 1H), 4.11–4.17 (tr, 2H), 4.45–4.50 (m, 1H), 6.78–6.84 (m, 2H), 7.09–7.14 (m, 2H), 7.19–7.25 (m, 2H), 7.29–7.34 (m, 2H). $^{13}$C-NMR (150 MHz; CDCl$_3$): δ 35.1, 37.3, 37.7, 53.6, 68.2, 114.8, 122.0, 127.8, 130.4, 130.5, 137.8, 147.6, 158.2, 170.0, 173.8.

Example 6

2-[4-(tert-Butoxycarbonylamino)phenyl]-1-ethanol 5 g (36 mmole) 4-aminophenethyl alcohol was dissolved in tetrahydrofuran and cooled on an icebath. 7.95 g (36 mmole) di-tert-butyl dicarbonate was added in portions. The reaction mixture was stirred at room temperature over night. The solvent was evaporated in vacuo to give 8 g (yield 94%) of 2-[4-(tert-butoxycarbonylamino)phenyl]-1-ethanol as a white powder.

4-(tert-Butoxycarbonylamino)phenethyl 3-nitro-benzenesulfonate 4.25 g (42 mmole) triethylamine was added to 10 g (42 mmole) 2-[4-(tert-butoxycarbonylamino)phenyl]-1-ethanol dissolved in dichloromethane. The reaction mixture was cooled to −25° C. and 9.34 g (42 mmole) 3-nitrobenzenesulfonyl chloride was added in portions. The reaction mixture was poured on to icewater, the phases were separated and the organic phase was dried (sodium sulfate), filtered and the solvent was evaporated in vacuo. The residue was purified by chromatography on silica gel using dichloromethane as eluent to give 8.3 g (yield 47%) 4-(tert-butoxycarbonylamino)-phenethyl 3-nitro-benzenesulfonate as yellow crystals.

tert-Butyl N-{4-[2-(4-formylphenoxy)ethyl]phenyl}carbamate 26.7 g (63 mmole) 4-(tert-butoxycarbonylamino) phenethyl 3-nitro-benzenesulfonate, 8.5 g (69 mmole) p-hydroxybenzaldehyde, 9.54 g (69 mmole) potassium carbonate and acetonitrile was refluxed for 3 hours and thereafter stirred over night at room temperature. The precipitate was filtered off and the solvent was evaporated. Dichloromethane was added and the organic phase was washed with saturated sodium carbonate and thereafter with sodium hydroxide (0.1 M), dried (sodium sulfate), filtered and the solvent was evaporated to give 17 g (yield 79%) of tert-butyl N-{4-[2-(4-formylphenoxy)ethyl]phenyl}carbamate.

4-[2-(4-Aminophenyl)ethoxy]benzaldehyde 5 g (14.6 mmole) tert-butyl N-{4-[2-(4-formylphenoxy)ethyl]phenyl}carbamate was deprotected in ethyl acetate saturated with hydrochloric acid at room temperature over night. The product precipitated and filtration yielded 5 g (100%) of 4-[2-(4-aminophenyl)ethoxy]benzaldehyde x HCl. The product contained some solvent, but was used without further purification.

N-{4-[2-(4-Formylphenoxy)ethyl]phenyl}methanesulfonamide 6.75 g (64 mmole) triethylamine was added to 5 g (14,6 mmole) 4-[2-(4-aminophenyl)ethoxy]benzaldehyde x HCl (containing some ethyl acetate) in dichloromethane. 3.65 g (32 mmole) methanesulfonyl chloride was slowly added at 0° C., and the mixture was stirred over the weekend. A yellow precipitate was filtered off and the filtrate was washed with water. The organic phase was dried (sodium sulfate), filtered and the solvent was evaporated. The residue contained some triethylamine and therefore it was dissolved in dichloromethane and washed with 2 M hydrochloric acid and brine, dried and filtered and the solvent was evaporated to give 1.6 g (yield 34%) of N-{4-[2-(4-formylphenoxy)ethyl]phenyl}methanesulfonamide as a yellow powder.

5-(4-[2-(4-Methanesulfonylaminophenyl)ethoxy]benzylidene)thiazolidine-2,4-dione 1.6 g (5 mmole) N-{4-[2-(4-formylphenoxy)ethyl]phenyl}methanesulfonamide, 0.73 g (6.25 mmole) 2,4-thiazolidinedione and 1.025 g (12.5 mmole) sodium acetate were mixed and heated to 140° C. on an oil bath under vacuum (it melted at 130° C.). It was kept at 140° C. for 20 minutes and thereafter taken off the heat. When the temperature was low enough water:acetone (2:1) was added to dissolve the reaction product. Acetone was evaporated in vacuo, acetic acid was added and the obtained crystals were filtered off and recrystallized in dichloromethane to give 0.83 g (yield 40%) of 5-(4-[2-(4-methanesulfonylaminophenyl)ethoxy]benzylidene)thiazolidine-2,4-dione.

$^1$H-NMR (400 MHz; acetone-d$_6$): δ 2.95 (s, 3H), 3.06–3.15 (tr, 2H), 4.25–4.34 (tr, 2H), 7.07–7.14 (m, 2H), 7.25–7.38 (m, 4H), 7.51–7.59 (m, 2H), 7.72 (s, 1H). $^{13}$C-NMR (100 MHz; acetone-d$_6$): δ 34.5, 38.05, 69, 115.5, 120.5, 121.5, 126, 130, 132, 132.5, 135, 137, 161, 167.5, 167.8.

5-([4-[2-(4-Methanesulfonylaminophenyl)ethoxy] phenyl]methyl)thiazolidine-2,4-dione 0.83 g (2 mmole) 5-(4-[2-(4-methanesulfonylaminophenyl)ethoxy]benzylidene) thiazolidine-2,4-dione and 0.65 g (2.6 mmole) diethyl-1,4-dihydro-2,6-dimethyl-3,5-pyridinedicarboxylate was mixed and heated to 145° C. under vacuum. After 45 minutes at 145° C. the reaction mixture was taken off the heat and toluene was added. The toluene solution was decanted off and the solid residue was purified by chromatography on silica gel using dichloromethane:methanol 95:5 as eluent to give 0.25 g (yield 30%) of the desired product.

$^1$H-NMR (400 MHz; acetone-d$_6$): δ 2.97 (s, 3H), 3.03–3.10 (tr, 2H), 3.10–3.19 (dd, 1H), 3.39–3.48 (dd, 1H), 4.16–4.24 (tr, 2H), 4.75–4.82 (dd, 1H), 6.87–6.94 (m, 2H), 7.19–7.26 (m, 2H), 7.26–7.39 (m, 4H), 8.5 (bs, 1NH). $^3$C-NMR (100 MHz; acetone-d$_6$): δ 35, 37, 39, 53, 69, 114.5, 120.7, 129, 130, 130.5, 135, 137, 158.5, 171, 175.

Example 7

5-(4-[2-(4-tert-Butyloxycarbonylaminophenyl) ethoxy]benzylidene)thiazolidine-2,4-dione A solution of 3.41 g (10 mmole) tert-butyl N-{4-[2-(4-formylphenoxy)ethyl]phenyl}carbamate and 1.29 g (11 mmole) 2,4-thiazolidinedione in toluene containing a catalytic amount of piperidinium acetate was refluxed in a Dean-Stark water trap for 3 hours. The reaction was followed by TLC and more 2,4-thiazolidinedione was added during the reaction time. The solution was cooled to room temperature filtered and the precipitate was refluxed in methanol. Another filtration gave 3.2 g (yield 72.6%) 5-(4-[2-(4-tert-butyloxycarbonylaminophenyl)ethoxy] benzylidene)thiazolidine-2,4-dione as a light yellow, solid substance.

$^1$H-NMR (500 MHz; DMSO-d$_6$): δ 1.5 (s, 9H), 2.89–3.10 (tr, 2H), 4.13–4.32 (tr, 2H), 7.01–7.16 (m, 2H), 7.16–7.32 (m, 2H), 7.32–7.49 (m, 2H), 7.49–7.66 (m, 2H), 7.76 (s, 1H), 9.3 (bs, 1NH). $^{13}$C-NMR (125 MHz; DMSO-d$_6$): δ 28.3, 34.3, 68.8, 79, 115.6, 118.4, 120.5, 125.7, 129.3, 131.7, 134.0, 132.3, 138.1, 153.0, 160.4, 167.7, 168.2.

5-(-[4-[2-(4-tert-Butyloxycarbonylaminophenyl) ethoxy]phenyl]methyl)thiazolidine-2,4-dione A solution of 0.5 g (1.14 mmole) 5-(4-[2-(4-tert-butyloxycarbonylaminophenyl)ethoxy]benzylidene) thiazolidine-2,4-dione in ethyl acetate was hydrogenated in the presence of 5% palladium on charcoal at room temperature and atmospheric pressure until hydrogen uptake ceased. The solution was filtered through celite, the filter pad was washed with ethyl acetate and the filtrate was evaporated to give 0.5 g (yield 99%) of 5-(-[4-[2-(4-tert-butyloxycarbonylaminophenyl)ethoxy]phenyl]methyl) thiazolidine-2,4-dione.

$^1$H-NMR (400 MHz; CDCl$_3$): δ 1.5 (s, 9H), 3.0–3.14 (m, 3H), 3.40–3.48 (dd, 1H), 4.08–4.16 (tr, 2H), 4.45–4.52 (dd, 1H), 6.55 (bs, 1NH), 6.79–6.87 (m, 2H), 7.08–7.15 (m, 2H), 7.15–7.23 (m, 2H), 7.23–7.34 (m, 2H).

Example 8

4-([3-Nitrophenylsulfonyl]oxy)phenethyl 3-nitrobenzenesulfonate 45 g (0.203 mole) 3-nitrobenzenesulfonyl chloride was added to a cooled solution of 13.8 g (0.1 mmole) p-hydroxyphenethyl alcohol and 25 g (0.248 mmole) triethylamine in 250 ml dichloromethane. The reaction mixture was stirred at room temperature for 1.5 hours. Dichloromethane and water were added and the phases separated. The organic phase was washed with dilute potassium hydrogen sulfate and water, dried (sodium sulfate), filtered and the solvent was evaporated in vacuo. Recrystallization in diisopropyl ether gave 48.8 g (yield 96%) of 4-([3-nitrophenylsulfonyl]oxy)phenethyl 3-nitrobenzenesulfonate.

4-[2-(4-Formylphenoxy)ethyl]phenyl 3-nitrobenzenesulfonate

A mixture of 32.5 g (64 mmole) 4-([3-nitrophenylsulfonyl]oxy)phenethyl 3-nitrobenzenesulfonate, 8 g (65 mmole) p-hydroxybenzaldehyde and 20 g (145 mmole) potassium carbonate in 300 ml acetonitrile was refluxed for 10 minutes, then stirred at room temperature over night and thereafter refluxed for 30 minutes. The salts were filtered off and the solvent evaporated in vacuo. Dichloromethane and water were added, the phases were separated, the organic phase was dried and the solvent was evaporated in vacuo. Purification by chromatography on silica gel using dichloromethane as eluent and crystallization in diisopropyl ether gave 23.5 g (yield 86%) of 4-[2-(4-formylphenoxy)ethyl] phenyl 3-nitrobenzenesulfonate.

5-(4-[2-(4-(3-Nitrophenylsulfonyloxy)phenyl) ethoxy]benzylidene)thiazolidine-2,4-dione 0.25 g (2.9 mmole) piperidine, 0.174 g (2.9 mmole) acetic acid, 120 ml toluene, 2.5 g (5.8 mmole) 4-[2-(4-formylphenoxy)ethyl]phenyl 3-nitrobenzenesulfonate and 0.86 g (7.3 mmole) 2,4-thiazolidinedione were refluxed with water separation in a Dean-Stark apparatus. When the reaction mixture was allowed to cool yellow crystals formed. The crystals were collected by filtration and stirred in methanol. Filtration gave 2 g (yield 65.5%) of 5-(4-[2-(4-(3-nitrophenylsulfonyloxy)phenyl)ethoxy]benzylidene) thiazolidine-2,4-dione.

$^1$H-NMR (400 MHz; DMSO-d$_6$): δ 2.99–3.10 (tr, 2H), 4.18–4.30 (t, 2H), 7.01–7.08 (m, 4H), 7.31–7.37 (d, 2H), 7.48–7.54 (d, 2H), 7.72 (s, 1H), 7.91–7.97 (tr, 1H), 8.23–8.28 (m, 1H), 8.44–8.48 (tr (long range), 1H), 8.59–8.64 (m, 1H). $^{13}$C-NMR (100 MHz; DMSO-d$_6$): δ 34.4, 68.5, 115.9, 120.9, 122.5, 123.4, 126.1, 130.0, 131.2, 132.21, 132,4, 132.5, 134.5, 136.2, 138.6, 147.8, 148.6, 160.5, 168.0, 168.4.

5-([4-[2-(4-(3-Nitrophenylsulfonyloxy)phenyl) ethoxy]phenyl]methyl)thiazolidine-2,4-dione 2,4 g (4.6 mmole) 5-(4-[2-(4-(3-nitrophenylsulfonyloxy) phenyl)ethoxy]benzylidene)thiazolidine-2,4-dione and 3.5 g (14 mmole) diethyl-1,4-dihydro-2,6-dimethyl-3,5-pyridine dicarboxylate were mixed and heated to 145° C. under vacuum and after 1–2 hours the heat was removed. The solid material was dissolved in toluene, evaporated in vacuo and purified by chromatography on silica gel twice with ethyl acetate:petroleum ether (1:1) as eluents to give 1.002 g (yield 41%) of the desired product.

$^1$H-NMR (300 MHz; CDCl$_3$): δ 2.92–3.15 (m, 3H), 3.35–3.55 (m, 1H), 4.0–4.25 (m, 2H), 4.40–4.55 (m, 1H), 6.65–6.85 (d, 2H), 6.85–7.0 (d, 2H), 7.0–7.15 (d, 2H), 7.15–7.33 (d, 2H), 7.67–7.83 (tr, 1H), 8.05–8.20 (d, 1H), 8.42–8.56 (d, 1H), 8.65 (s, 1H). $^{13}$C-NMR (75 MHz; CDCl$_3$): δ 35.0, 37.7, 53.8, 68.1, 114.8, 122.0, 123.7, 128.0, 128.7, 130.4, 130.6, 130.8, 133.9, 137.4, 138.3, 147.7, 148.2, 158.0, 171.1, 174.8.

Example 9

2-(Methylsulfonyloxy)phenethyl methanesulfonate 9 g (79 mmole) methanesulfonyl chloride in dichloromethane was slowly added to a mixture of 5 g (36 mmole) o-hydroxyphenethyl alcohol and 7.99 g (79 mmole) triethylamine in dichloromethane at 0–10° C. The temperature was then allowed to raise to room temperature and when the starting material was consumed the reaction mixture was poured on to hydrochloric acid/ice water. The phases were separated and the organic phase was washed with brine, dried and evaporated in vacuo. The residue crystallized on standing to give 9.4 g (yield 89%) yellow crystals of 2-(methylsulfonyloxy)phenethyl methanesulfonate.

2-[2-(4-Formylphenoxy)ethyl]phenyl methanesulfonate 9.2 g (31 mmole) 2-(methylsulfonyloxy)phenethyl methanesulfonate, 4.58 g (37.5 mmole) p-hydroxybenzaldehyde and 5.18 g (37.5 mmole) potassium carbonate were refluxed in acetonitrile for 4 hours and then stirred at room temperature over night. The salts were filtered off and the solvent was evaporated in vacuo. Sodium carbonate solution and dichloromethane was added to the residue. The phases were separated and the organic phase was dried and evaporated in vacuo. Chromatography on silica gel using dichloromethane as eluent gave a mixture of starting material and product. The reaction was restarted with 4.58 g p-hydroxybenzaldehyde and 5.18 g potassium carbonate and worked up as above to give 1.7 g of pure 2-[2-(4-formnylphenoxy)ethyl]phenyl methanesulfonate.

5-(4-[2-(2-Methanesulfonyloxyphenyl)ethoxy]benzylidene)thiazolidine-2,4-dione 1.7 g (5.3 mmole) 2-[2-(4-formylphenoxy)ethyl]phenyl methanesulfonate, 0.77 g (6.6 mmole) 2,4-thiazolidinedione and 1.06 g (13.2 mmole) sodium acetate were heated to 130° C. and allowed to stay at 130° C. for 10 minutes. The reaction mixture was taken off the heat and water:acetone (2:1) was added, the formed solid material was stirred with water and acetic acid, the precipitate was collected by filtration and washed with diethyl ether and recrystallized in dichloromethane to give 1.63 g (yield 61%) of 5-(4-[2-(2-methanesulfonyloxyphenyl)ethoxy]benzylidene)thiazolidine-2,4-dione.

$^1$H-NMR (500 MHz; DMSO-$d_6$): δ 3.09–3.22 (tr, 2H), 3.49 (s, 3H), 4.23–4.39 (tr, 2H), 7.02–7.17 (m, 2H), 7.28–7.42 (m, 3H), 7.42–7.59 (m, 3H), 7.63 (s, 1H).

5-([4-[2-(2-Methanesulfonyloxyphenyl)ethoxy]phenyl]methyl)thiazolidine-2,4-dione 1.63 g (3.2 mmole) 5-(4-[2-(2 methanesulfonyloxyphenyl)ethoxy]benzylidene)thiazolidine-2,4-dione and 1.23 g (4.8 mmole) diethyl-1,4-dihydro-2,6-dimethyl-3,5-pyridine dicarboxylate was mixed and heated to 150° C. and kept at this temperature for 1 hour. The reaction mixture was cooled and purified by chromatography on silica gel using ethyl acetate:petroleum ether (1:2) as eluent to give 0.684 g (yield 51%) of the desired product.

$^1$H-NMR (400 MHz; CDCl$_3$): δ 3.03–3.15 (m, 1H), 3.15–3.26 (m, 5H), 3.38–3.48 (m, 1H), 4.16–4.23 (tr, 2H), 4.43–4.52 (m, 1H), 6.79–6.89 (d, 2H), 7.08–7.16 (d, 2H), 7.22–7.44 (m, 4H). $^{13}$C-NMR (100 MHz; DMSO-$d_6$): δ 30.0, 37.7, 38.3, 53.7, 67.2, 122.2, 114.9, 127.4, 128.0, 128.2, 130.4, 131.4, 131.6, 147.7, 158.1, 170.8, 174.5.

Example 10

N-[4-(2-Hydroxyethyl)phenyl]-N$^1$-methylurea 34.3 (0.25 mole) p-aminophenethyl alcohol and 20 g (0.35 mmole) methyl isocyanate in 400 ml tetrahydrofuran was mixed and the formed white precipitate was collected by filtration to give 44.87 (yield 92.4%) of N-[4-(2-hydroxyethyl)phenyl]-N$^1$-methylurea.

4-(Methylaminocarbonylamino)phenethyl methanesulfonate 47 g (0.412 mole) methanesulfonyl chloride in dichloromethane was added in small portions to a solution of 20 g (0.103 mole) N-[4-(2-hydroxyethyl)phenyl]-N$^1$-methylurea and 41.7 g (0.412 mole) triethylamine in 500 ml dichloromethane at 0° C. After stirring at room temperature over night the reaction mixture was washed with 2 M hydrochloric acid and sodium bicarbonate. The organic phase was dried and concentrated by evaporation in vacuo and the formed precipitate was collected by filtration to give 8.81 g (yield 31%) of 4-(methylaminocarbonylamino)phenethyl methanesulfonate.

4-[2-(4-Formylphenoxy)ethyl]phenyl methylurea 2 g (7.3 mmole) 4-(methylaminocarbonylamino) phenethyl methanesulfonate, 1.08 g (8.8 mmole) p-hydroxybenzaldehyde and 1.22 g (8.8 mmole) potassium carbonate in acetonitrile were refluxed over night. The salts were filtered off and the solvent was evaporated. The residue was dissolved in dichloromethane, washed with 2 M sodium hydroxide, dried and evaporated in vacuo. The solid residue was dissolved in water and acidified with 2 M hydrochloric acid, diethyl ether was added and the formed precipitate was collected by filtration to give 1 g (yield 46%) of 4-[2-(4-fornylphenoxy)ethyl]phenyl methylurea.

5-(4-[2-(4-Methylureidophenyl)ethoxy]benzylidene)thiazolidine-2,4-dione 3.5 g (12 mmole) 4-[2-(4-fornylphenoxy)ethyl]phenyl methylurea, 3.44 (29 mmole) 2,4-thiazolidinedione, 0.1 g piperidine, 0.07 g acetic acid and toluene were refluxed with water separation in a Dean-Stark apparatus. When the reaction mixture was cooled to room temperature the formed precipitate was collected and washed with methanol to give 4.25 g (yield 89%) of 5-(4-[2-(4-methylureidophenyl)ethoxy]benzylidene)thiazolidine-2,4-dione.

$^1$H-NMR (300 MHz; DMSO-$d_6$): δ 2.55–2.65 (d, 3H), 2.85–3.0 (tr, 2H), 4.1–4.3 (tr, 2H), 5.9–6.1 (m, 1NH), 7.02–7.22 (m, 4H), 7.22–7.42 (m, 2H), 7.42–7.61 (m, 2H), 7.73 (s, 1NH), 8.42 (s, 1NH). $^{13}$C-NMR (75 MHz; DMSO-$d_6$): δ 26.1, 34.0, 68.5, 115.2, 117.6, 120.2, 125.3, 129.0, 130.2, 131.7, 132.0, 138.9, 155.8, 160.1, 167.4, 167.9.

5-([4-[2-(4-Methylureidophenyl)ethoxy]phenyl]methyl)thiazolidine-2,4-dione 1.2 g (3.02 mmole) 5-(4-[2-(4-methylureidophenyl) ethoxy]benzylidene)thiazolidine-2,4-dione was hydrogenated for 18 hours in 100 ml dimethylformamide and 10 ml acetic acid with 1 g Pd/C (10%) as catalyst. The catalyst was filtered off and the solvent was evaporated in vacuo. Ethyl acetate was added and the product was extracted with potassium carbonate in water. A black precipitate was filtered off and the ethyl acetate phase was extracted with more potassium carbonate solution. The water phase was acidified with dilute hydrochloric acid and extracted with ethyl acetate. The organic phase was dried and evaporated in vacuo and recrystallized in methanol to give 0.71 g (yield 59%) of the desired product.

$^1$H-NMR (300 MHz; DMSO-$d_6$): δ 2.55–2.71 (d, 3H), 2.8–3.12 (m, 3H), 3.2–3.38 (m, 1H), 3.98–4.19 (tr, 2H), 4.75–4.92 (m, 1H), 5.84–6.0 (m, 1NH), 6.77–6.93 (m, 2H), 6.98–7.2 (m, 4H), 7.2–7.4 (m, 2H), 8.38 (s, 1NH), 12.01 (bs, 1NH). $^{13}$C-NMR (125 MHz; DMSO-$d_6$): δ 26.4, 34.5, 36.5, 53.2, 68.5, 114.5, 118.0, 128.7, 129.3, 130.6, 130.8, 139.1, 156.1, 157.7, 171.9, 175.9.

Example 11

4-[2-(4-Acetylphenoxy)ethyl]phenyl methanesulfonate 13.6 g (0.1 mole) p-hydroxyacetophenone, 29.4 g (0.1 mole) 4-(methylsulfonyloxy)phenethyl methanesulfonate and 42.4 g (0.3 mole) potassium carbonate in acetonitrile were refluxed over night. The salts were filtered off and the solvent was evaporated in vacuo. The residue was crystallized in isopropyl alcohol. The crystals were dissolved in dichloromethane, washed with diluted potassium carbonate, dried (magnesium sulfate), filtered and evaporated to give 22.7 g (yield 68%) 4-[2-(4-acetylphenoxy)ethyl]phenyl methanesulfonate.

5-(1-[4-[2-(4-Methanesulfonyloxyphenyl)ethoxy]phenyl]ethylene)thiazolidine-2,4-dione 10 g (29.9 mmole) 4-[2-(4-acetylphenoxy)ethyl]phenyl methanesulfonate and 3.85 g (32.9 mmole) 2,4-thiazolidinedione were heated to 140° C. when the reaction mixture melted. 4.76 g (38 mmole) sodium acetate was added and the reaction mixture was stirred under vacuum at elevated temperature until the reaction mixture was solid again. The heat was removed, water and acetone was added, acetone was evaporated in vacuo, and acidification with acetic acid gave crystals that were collected and recrystallized in acetic acid to give 5 g (yield 39%) of 5-(1-[4-[2-(4-methanesulfonyloxyphenyl)ethoxy]phenyl]ethylene) thiazolidine-2,4-dione.

$^1$H-NMR (300 MHz; DMSO-$d_6$): δ 2.65 (s, 3H), 3.00–3.15 (t, 2H), 3.38 (s, 3H), 4.15–4,35 (t, 2H), 6.95–7.1 (d, 2H), 7.25–7.32 (d, 2H), 7.32–7.42 (d, 2H), 7.45–7.5 (d, 2H), 12.25 (bs, 1H). $^{13}$C-NMR (75 MHz; DMSO-$d_6$): δ 21.6, 34.3, 37.5, 68.2, 114.9, 121.5, 122.3, 128.7, 130.8, 134.5, 137.8, 147.9, 149.1, 159.2, 167.3, 168.2.

5-(1-[4-[2-(4-Methanesulfonyloxyphenyl)ethoxy]phenyl]ethyl)thiazolidine-2,4-dione 2.8 g (6.4 mmole) 5-(1-[4-[2-(4-methanesulfonyloxyphenyl)ethoxy]phenyl]ethylene) thiazolidine-2,4-dione and 1.6 g (6.4 mmole) diethyl-1,4-dihydro-2,6-dimethyl-3,5-pyridine dicarboxylate was mixed and heated to 170° C. under vacuum. After 4 hours at 170° C. the reaction mixture was taken off the heat, cooled to room temperature and purified by chromatography on silica gel using ethyl acetate and dichloromethane gradient as eluent to give 0.8 g (yield 29%) of a diastereomeric mixture of the desired product.

$^1$H-NMR (300 MHz; DMSO-$d_6$): δ 1.2–1.4 (2 x d(diastereomers), 3H), 2.95–3.15 (tr,2H), 3.35 (s, 3H), 3.5–3.7 (2 x m(diastereomers), 1H), 4.1–4.25 (tr, 2H), 4.82–4.95 (m, 1H), 6.8–6.95 (m, 2H), 7.1–7.23 (m, 2H), 7.23–7.34 (m, 2H), 7.34–7.5 (m, 2H).

Example 12

2-(4-Methylcarbonyloxyphenyl)-1-ethanol 5.6 g (0.1 mole) potassium hydroxide in 10 ml water was added to a cooled solution of 13.8 g (0.1 mole) p-hydroxyphenethyl alcohol in 50 ml tetrahydrofuran. 10.2 g (0.1 mole) acetic anhydride was slowly added under stirring. After 2 hours diethyl ether and water were added. The phases were separated and the organic phase was dried, filtered and evaporated in vacuo. The product contained 15% starting material and was therefore redissolved in diethyl ether and washed twice with dilute sodium carbonate. Drying, filtration and evaporation of solvents in vacuo gave 12 g (yield 67%) of 2-(4-methylcarbonyloxyphenyl)-1-ethanol which was used without further purification.

4-(Methylcarbonyloxy)phenethyl methanesulfonate 55 g (0.305 mole) 2-(4-methylcarbonyloxyphenyl)-1-ethanol and 34.4 g (0.341 mole) triethylamine in 300 ml dichloromethane were cooled on an ice bath. 38.5 g (0.336 mole) methanesulfonyl chloride was slowly added. The ice bath was removed and the mixture was stirred for 3 hours at room temperature. Water was added and the phases were separated. The organic phase was washed with saturated sodium hydrogen bicarbonate and brine, dried (magnesium sulfate), filtered and evaporated in vacuo to give 76.6 g (yield 97%) of 4-(methylcarbonyloxy)phenethyl methanesulfonate.

4-[2-(4-Formylphenoxy)ethyl]phenyl acetate 10.3 g (39.9 mmole) 4-(methylcarbonyloxy)phenetyl methanesulfonate, 5.37 g (44 mmole) p-hydroxybenzaldehyde and 10 g (72.5 mmole) potassium hydroxide were refluxed in 100 ml acetonitrile for 2 hours. The salts were filtered off and the solvents was evaporated. The residue was dissolved in ethyl acetate and washed with water 3 times, dried and evaporated in vacuo to give 10.8 g (yield 95%) of 4-[2-(4-formylphenoxy)ethyl]phenyl acetate.

4-[2-(4-Hydroxyphenyl)ethoxy]benzaldehyde

Ammonium hydroxide was added to a solution of 2.0 g (7 mmole) 4-[2-(4-formylphenoxy)ethyl]phenyl acetate in methanol. When the starting material was consumed the solvent was evaporated in vacuo. 0.5 M hydrochloric acid was added and the product was extracted with diethyl ether and dichloromethane, dried, filtered and evaporated to give 1.6 g (yield 93%) of 4-[2-(4-hydroxyphenyl)ethoxy] benzaldehyde $^1$H-NMR (400 MHz; DMSO-$d_6$): δ 2.95–3.05 (tr, 2H), 4.22–4.32 (tr, 2H), 6.72–6.78 (m, 2H), 7.1–7.2 (m, 4H), 7.88–7.94 (m, 2H), 9.23 (s, 1H), 9.91 (s, 1H) $^{13}$C-NMR (100 MHz; DMSO-$d_6$): δ 34.4, 69.5, 115.4, 115.6, 130.3, 132.2, 156.4, 164.0.

4-[2-(4-Formnylphenoxy)ethyl]phenyl N-(tert-butyl) carbamate 0.5 g (2.1 mmole) 4-[2-(4-hydroxyphenyl)ethoxy] benzaldehyde was dissolved in tetrahydrofuran, cooled to 0° C. and 0.092 g (2.1 mmole) sodium hydride in tetrahydrofuiran was added. The reaction mixture was stirred until gas development ceased, then 0.4 g (4 mmole) tert-butyl isocyanate in tetrahydrofuran was added and the temperature was allowed to rise to room temperature. The reaction was followed by TLC. More 0.4 g (4 mmole) tert-butyl isocyanate was added. After 3 days the reaction was quenched with ice and sodium hydroxide (aq), extracted with dichloromethane, dried and evaporated. Purification by chromatography on silica gel using ethyl acetate:petroleum ether (1:2) as eluent gave 0.6 g (yield 84%) of 4-[2-(4-formylphenoxy)ethyl]phenyl N-(tert-butyl)carbamate.

5-(4-[2-(4-tert-Butylaminocarbonyloxyphenyl) ethoxy]benzylidene)thiazolidine-2,4-dione 3.5 g (10.2 mmole) 4-[2-(4-formylphenoxy)ethyl]phenyl N-(tert-butyl)carbamate, 3 g (25.5 mmole) 2,4-thiazolidindione, 0.1 g piperidine and 0.07 g acetic acid in toluene was refluxed with water separation in a Dean-Stark apparatus. The solvent was evaporated in vacuo, acetone and water was added and the formed precipitate was filtered off to give 2 g (yield 45%) of 5-(4-[2-(4-tert-butylaminocarbonyloxyphenyl)ethoxy]benzylidene) thiazolidine-2,4-dione.

$^1$H-NMR (500 MHz; DMSO-$d_6$): δ 1.24 (s, 9H), 2.96–3.07 (tr, 2H), 4.18–4.28 (tr, 2H), 6.95–7.0 (m, 2H), 7.04–7.1 (m, 2H), 7.25–7.3 (m, 2H), 7.47 (s, 1H), 7.48–7.53 (m, 2H), 7.7 (s, 1NH).

5-([4-[2-(4-tert-Butylaminocarbonyloxyphenyl) ethoxy]phenyl]methyl)thiazolidine-2,4-dione 1 g (2.27 mmole) 5-(4-[2-(4-tert-butylaminocarbonyloxyphenyl)ethoxy]benzylidene) thiazolidine-2,4-dione was hydrogenated on Pd/C (5%) in ethyl acetate at atmospheric pressure over night. The catalyst was filtered off and the solvent was evaporated in vacuo to give 1 g (yield 99%) of the desired product.

$^1$H-NMR (400 MHz; DMSO-$d_6$): δ 1.25 (s, 9H), 2.95–3.08 (m, 3H), 3.23–3.34 (m, 1H), 4.08–4.17 (tr, 2H), 4.30–4.38 (m, 1H), 6.83–6.89 (m, 2H), 6.95–7.01 (m, 2H), 7.09–7.15 (m, 2H), 7.25–7.31 (m, 2H), 7.49 (s, 1NH), 12.01 (bs, 1H). $^{13}$C-NMR (100 MHz; DMSO-$d_6$): δ 28.9, 34.7, 36.8, 50.2, 53.5, 68.5, 114.8, 122.2, 129.1, 130.1, 130.8, 135.2, 150.0, 153.2, 157.9, 172.1, 176.2.

Example 13

Methyl N-[4-(2-hydroxyethyl)phenyl]carbamate 9.45 g (0.1 mole) methylchloroformate was added to a solution of 13.72 g (0.1 mole) p-aminophenethyl alcohol and 8.4 g (0.1 mole) pyridine in dichloromethane at 0° C. The reaction was stirred between 0° C. and room temperature, and when completed, poured onto ice water and the product was extracted with ethyl acetate, dried and the solvent was evaporated in vacuo to give 6.7 g (yield 34.7%) of methyl N-[4-(2-hydroxyethyl)phenyl]carbamate.

4-[(Methoxycarbonyl)amino]phenethyl methanesulfonate 6.0 g (30.7 mmole) methyl N-[4-(2-hydroxyethyl)phenyl] carbamate was dissolved in acetonitrile. 6.17 g (61 mmole) triethylamine and 7.0 g (61 mmole) methanesulfonyl chloride were added. The mixture was stirred until completion, then the solvent was evaporated in vacuo, water was added to the residue and the product was extracted with dichloromethane to give 7.5 g (yield 89.4%) of 4-[(methoxycarbonyl)amino]phenethyl methanesulfonate.

Methyl N-{4-[2-(4-formylphenoxy)ethyl] phenyl}carbamate 7 g (26 mmole) 4-[(methoxycarbonyl)amino]phenethyl methanesulfonate, 6.2 g (51 mmole) 4-hydroxybenzaldehyde and 7.05 g potassium carbonate in acetonitrile was refluxed for 3 h. The solvent was evaporated in vacuo, 1 M sodium hydroxide was added and the product was extracted with dichloromethane, washed with brine, dried and the solvent was evaporated. The reaction was not completed and therfore restarted with 3.1 g 4-hydroxybenzaldehyde and 3.5 g potassium carbonate in acetonitrile and refluxed for 4 h. The solvent was evaporated and the residue was stirrred in dichloromethane over night. The precipitate was filtered off and the solvent was evaporated to give 5.9 g (yield 75.8%) of methyl N-{4-[2-(4-formylphenoxy)ethyl]phenyl}carbamate wich was used without further purification.

5-(4-[2-(4-Methoxycarbonylaminophenyl)ethoxy] benzylidene)thiazolidine-2,4-dione 2 g (6.7 mmole) methyl N-{4-[2-(4-formylphenoxy)ethyl] phenyl}carbamate, 1.57 g (13.4 mmole) 2,4-thiazolidinedione, piperidine, acetic acid and toluene were refluxed with water separation in a Dean-Stark apparatus for 3 hours. The formed yellow precipitate was collected by filtration giving 1.9 g (yield 71.2%) of 5-(4-[2-(4-methoxycarbonylaminophenyl)ethoxy]benzylidene) thiazolidine-2,4-dione.

$^1$H-NMR (400 MHz; DMSO-$d_6$): δ 2.92–2.98 (tr, 2H), 3.63 (s, 3H), 4.16–4.22 (tr, 2H), 7.03–7.08 (d, 2H), 7.17–7.23 (d, 2H), 7.34–7.40 (d, 2H), 7.47–7.53 (d, 2H), 7.21 (s, 1H), 9.54 (s, 1 NH), 12,46 (s, 1 NH). $^{13}$C-NMR (100 MHz; DMSO-$d_6$): δ 34.5, 52.0, 69.0, 115.8, 118.8, 120.7, 125.9, 129.7, 132.3, 132,4, 132.6, 138.0, 154.5, 160.6, 167.9, 168.4.

5-([4-[2-(4-Methoxycarbonylaminophenyl)ethoxy] phenyl]methyl)thiazolidine-2,4-dione 1 g (2.5 mmole) 5-(4-[2-(4-methoxycarbonylaminophenyl)ethoxy]benzylidene) thiazolidine-2,4-dione was mixed with Pd/C (5%) and hydrogenated in ethyl acetate for 4 hours at room temperature. The catalyst was filtered off through celite and the solvent was evaporated in vacuo. All of the starting material was not consumed so the hydrogenation was restarted as above. The catalyst was filtered off through celite and the solvent was evaporated in vacuo. The crude product was purified by crystallization in diethyl ether to give 0.47 g (yield 47%) of the desired product.

$^1$H-NMR (400 MHz; DMSO-$d_6$): δ 2.89–2.97 (tr, 2H), 2.98–3.08 (m, 1H), 3.23–3.33 (m, 1H), 3.36 (s, 3H), 4.06–4.13 (tr, 2H), 4.80–4.89 (m, 1H), 6.81–6.89 (d, 2H), 7.16–7.24 (d, 2H), 7.33–7.41 (d, 2H), 9.53 (s, 1 NH), 11.97 (s, 1 NH). $^{13}$C-NMR (100 MHz; DMSO-$d_6$): δ 34.8, 36.8, 52.0, 53.5, 68.6, 114.8, 118.7, 129.1, 129.7, 130.8, 132.7, 137.9, 154.5, 158.0, 172.1, 176.2.

Example 14

4-{2-[4-(Hydroxyiminomethyl)phenoxy] ethyl}phenyl methanesulfonate 3.52 g (11 mmole) 4-[2-(4-formylphenoxy)ethyl]phenyl methanesulfonate was dissolved in 150 ml ethanol. 2.29 g (33 mmole) hydroxylamine hydrochloride and 3.6 g (44 mmole) sodium acetate in 30 ml water were added. The reaction mixture was stirred at 50° C. for 1 h 45 minutes. The solvent was evaporated in vacuo and water was added to give a white precipitate, which was filtered off and washed with hexane to give 3.3 g (yield 89%) of 4-{2-[4-(hydroxyiminomethyl)phenoxy]ethyl}phenyl methanesulfonate.

¹H-NMR (300 MHz; DMSO-d₆): δ 3.01–3.12 (tr, 2H), 3.35 (s, 3H), 4.16–4.27 (tr, 2H), 6.9–7.0 (d, 2H), 7.25–7.33 (d, 2H), 7.39–7.54 (m, 4H), 8.04 (s, 1H), 10.92 (s, 1H). ¹³C-NMR (75 MHz; DMSO-d₆): δ 34.0, 37.2, 67.8, 114.6, 122.0, 125.6, 127.7, 130.5, 132.2, 137.6, 147.5, 159.1.

4-(2-{4-[Hydroxyaminomethyl]phenoxy}ethyl) phenyl methanesulfonate 1.88 g (30 mmole) sodium cyanoborohydride was added to a solution of 2.0 g (6 mmole) 4-{2-[4-(hydroxyiminomethyl)phenoxy]ethyl}phenyl methanesulfonate in 90 ml methanol and 18 ml tetrahydrofuran. Gas evolution was observed. 5 mg methyl orange was added resulting in a yellow colour. 4 M hydrochloric acid:dioxane (2:1) was added dropwise until the color was dark red (pH 2–3). The reaction mixture was poured into water, basified with 2 M sodium hydroxide (pH 9). More water was added and the product was extracted with ethyl acetate, dried, filtered and evaporated. The yellow residue was purified by chromatography on silica gel using ethyl acetate as eluent to give 1.2 g colourless oil of 4-(2-{4-[hydroxyaminomethyl]phenoxy}ethyl)phenyl methanesulfonate.

¹H-NMR (400 MHz; CDCl₃): δ 3.04–3.12 (m, 5H), 3.88 (s, 2H), 4.16–4.21 (tr, 2H), 5.3 (bs, 1H), 6.86–6.90 (m, 2H), 7.18–7.38 (m, 6H). ¹³C-NMR (100 MHz; CDCl₃): δ 35.1, 37.3, 57.5, 68.3, 114.6, 122.0, 129.3, 130.5, 130.6, 137.9, 147.9, 158.2.

2-([4-[2-(4-Methanesulfonyloxyphenyl)ethoxy] phenyl]methyl) 1,2,4-oxadiazolidine-3,5-dione 0.45 g (4 mmole) N-(chlorocarbonyl)isocyanate was added dropwise to a solution of 1.2 g (3.6 ml) 4-(2-{4-[hydroxyaminomethyl]phenoxy}ethyl)phenyl methanesulfonate in 20 ml anhydrous tetrahydrofuran at −5° C. and the mixture was stirred at −5° C. for 30 minutes. The reaction mixture was poured on to 2 M hydrochloric acid and extracted with ethyl acetate, dried (sodium sulfate), filtered and evaporated in vacuo. The residue was redissolved in ethyl acetate, and material that did not go into solution was filtered off. The filtrate was evaporated in vacuo, diethyl ether was added to give a white precipitate which was filtered off and recrystallized in diethyl ether/acetone to give 0.223 g of the desired product. The mother liquid was evaporated in vacuo and purified by chromatography on silica gel using dichloromethane:methanol (95:5) as eluent and crystallized in diethyl ether to give 0.09 g more of the desired product (total yield 0.384 g, 26.2%).

¹H-NMR (500 MHz; DMSO-d₆): δ 3.04–3.10 (tr, 2H), 3.36 (s, 3H), 4.18–4.24 (tr, 2H), 4.72 (s, 2H), 6.94–6.99 (d, 2H), 7.23–7.32 (m, 4H), 7.42–7.46 (d, 2H), 12.41 (bs, 1H). ¹³C-NMR (125 MHz; DMSO-d₆): δ 34.4, 37.5, 52.6, 68.0, 114.8, 122.3, 126.1, 130.3, 130.7, 137.9, 147.8, 152.6, 158.2, 158.5.

Example 15

4-[2-(4-Formylphenoxy)ethyl]phenyl 2-propanesulfonate 3.77 g (13 mmole) 2-propanesulfonyl chloride dissolved in dichloromethane was slowly added to a solution of 3.2 g (13 mmole) 4-[2-(4-hydroxyphenyl)ethoxy]benzaldehyde and 2.63 g (26 mmole) triethylamine in 80 ml dichloromethane at 0° C. The temperature was slowly allowed to rise to room temperature and when the starting material was consumed the reaction mixture was poured on to ice. The phases were separated and the organic phase was washed with sodium carbonate, dried (sodium sulfate), filtered and evaporated. The residue was purified by chromatography on silica gel using dichloromethane as eluent to give 3.3 g (yield 72.8%) of 4-[2-(4-formylphenoxy)ethyl]phenyl 2-propanesulfonate.

¹H-NMR (500 MHz; CDCl₃): δ 1.57–1.61 (d, 6H), 3.15–3.20 (tr, 2H), 3.46–3.56 (sept, 1H), 4.26–4.31 (tr, 2H), 7.00–7.05 (m, 2H), 7.25–7.29 (m, 2H), 7.34–7.38 (m, 2H), 7.83–7.88 (m, 2H), 9.92 (s, 1H). ¹³C-NMR (125 MHz; CDCl₃): δ 16.5, 34.7, 52.2, 68.4, 114.5, 121.9, 129.9, 130.2, 131.8, 136.6, 147.5, 163.6, 190.5.

5-(4-[2-(4-(2-Propanesulfonyloxy)phenyl)ethoxy] benzylidene)thiazolidine-2,4-dione 1.4 g (4 mmole) 4-[2-(4-formylphenoxy)ethyl]phenyl 2-propanesulfonate, 0.94 (8 mmole) 2,4-thiazolidinedione, 5 drops of piperidine, 6 drops of acetic acid and toluene were refluxed with water separation in a Dean-Stark apparatus. When the starting material was consumed the heat was removed and the formed crystals were recrystallized in water:acetone to give 1.5 g (yield 58.6%) of 5-(4-[2-(4-(2-propanesulfonyloxy)phenyl)ethoxy]benzylidene)thiazolidine-2,4-dione.

¹H-NMR (500 MHz; DMSO-d₆): δ 1.40–1.44 (d, 6H), 3.05–3.12 (tr, 2H), 3.65–3.74 (sept, 1H), 4.26–4.32 (tr, 2H), 7.08–7.13 (m, 2H), 7.23–7.28 (m, 2H), 7.41–7.46 (m, 2H), 7.52–7.56 (m, 2H), 7.74 (s, 1H), 12.51 (bs, NH). ¹³C-NMR (125 MHz; DMSO-d₆): δ 16.5, 34.7, 52.2, 68.4, 114.5, 121.9, 129.9, 130.2, 131.8, 136.6, 147.5, 163.6, 190.5.

5-([4-[2-(4-(2-Propanesulfonyloxy)phenyl)ethoxy] phenyl]methyl)thiazolidine-2,4-dione 1.2 g (2.7 mmole) 5-(4-[2-(4-(2-propanesulfonyloxy) phenyl)ethoxy]benzylidene)thiazolidine-2,4-dione was dissolved in 250 ml ethyl acetate by heating. 6 ml acetic acid and 1 g Pd/C (5%) were added and the hydrogenation was started while the solution was warm. After 12 hours at room temperature, more of the catalyst was added. After 60 hours the reaction mixture was filtered through celite and the solvent was evaporated in vacuo. The hydrogenation was restarted with more Pd/C (10%) and ethyl acetate. After 6 hours the reaction mixture was filtered through celite and the solvent was evaporated in vacuo. The crude product was purified by chromatography on silica gel using dichloromethane:methanol (95:5) as eluent to give 0.557 g (yield 45.9%) of the desired product.

¹H-NMR (400 MHz; CDCl₃): δ 1.54–1.58 (d, 6H), 3.06–3.14 (m, 3H), 3.41–3.54 (m, 2H), 4.12–4.19 (tr, 2H), 4.47–4.53 (m, 1H), 6.82–6.87, (m, 2H), 7.11–7.17 (m, 2H), 1.19–7.25 (m, 2H), 7.29–7.35 (m, 2H). ¹³C-NMR (100 MHz; CDCl₃): δ 16.8, 35.1, 37.8, 52.5, 53.7, 68.3, 114.9, 122.0, 128.0, 130.38, 130.42, 137.3, 148.0, 158.4, 170.3, 174.3.

Example 16

4-[Phenylsulfonyl)oxy]phenethyl 1-benzenesulfonate 42.2 g (240 mmole) benzenesulfonyl chloride in dichloromethane was slowly added to a solution of 15 g (108 mmole) 4-hydroxyphenethyl alcohol and 24.3 g (240 mmole) triethylamine in 120 ml dichloromethane at 0° C. After stirring at 0° C. to room temperature the starting material was consumed, water was added, the phases were separated and the organic phase was evaporated in vacuo.

Diisopropyl ether was added, two phases were formed, the diisopropyl ether phase was decanted off and the rest of solvent was evaporated to give 32.65 g (yield 73%) of 4-[phenylsulfonyloxy]phenethyl 1-benzenesulfonate.

$^1$H-NMR (300 MHz; CDCl$_3$): δ 2.84–2.94 (tr, 2H), 4.12–4.24 (tr, 2H), 6.78–6.88 (m, 2H), 6.96–7.04 (m, 2H), 7.40–7.83 (m, 10H).

4-[2-(4-Formylphenoxy)ethyl]phenyl 1-benzenesulfonate 20 g (48 mmole) 4-[phenylsulfonyloxy]phenethyl 1-benzenesulfonate, 11.7 g (95 mmole) p-hydroxybenzaldehyde and 13.27 g (96 mmole) potassium carbonate in 100 ml acetonitrile were refluxed over night. The precipitate was filtered off and the filtrate was evaporated in vacuo. Dichloromethane was added, the solid material was filtered off and the filtrate was evaporated in vacuo. The residue was purified by chromatography on silica gel using ethyl acetate:petroleum ether (1:2) as eluent to give 12 g (yield 65%) of 4-[2-(4-formylphenoxy)ethyl]phenyl 1-benzenesulfonate.

$^1$H-NMR (500 MHz; CDCl$_3$): δ 3.05–3.10 (tr, 2H), 4.18–4.24 (tr, 2H), 6.90–6.98 (m, 4H), 7.18–7.23 (m, 2H), 7.43–7.54 (m, 2H), 7.63–7.69 (m, 1H), 7.78–7.84 (m, 4H), 9.86 (s, 1H). $^{13}$C-NMR (125 MHz; CDCl$_3$): δ 34.6, 68.2, 114.5, 122.1, 128.1, 128.9, 129.8, 129.9, 131.7, 134.0, 135.1, 136.9, 148.0, 163.4, 190.5.

5-(4-[2-(4-(Benzenesulfonyloxy)phenyl)ethoxy]benzylidene)thiazolidine-2,4-dione 2.0 g (5.2 mmole) 4-[2-(4-fornylphenoxy)ethyl]phenyl 1-benzenesulfonate, 1.53 g (13 mmole) 2,4-thiazolidinedione, 5 drops of piperidine and 6 drops of acetic acid in toluene were refluxed with water separation in a Dean-Stark apparatus. When the reaction mixture was cooled to room temperature a precipitate was formed and filtered off to give 1.5 g (yield 60%) of 5-(4-[2-(4-(benzenesulfonyloxy)phenyl)ethoxy]benzylidene)thiazolidine-2,4-dione.

$^1$H-NMR (500 MHz; DMSO-d$_6$): δ 2.99–3.07 (tr, 2H), 4.21–4.28 (tr, 2H), 6.93–6.99 (m, 2H), 7.05–7.10 (m, 2H), 7.30–7.36 (m, 2H), 7.50–7.55 (m, 2H), 7.63–7.70 (m, 2H), 7.73 (s, 1H), 7.78–7.9 (m, 3H), 12.5 (s, NH). $^{13}$C-NMR (125 MHz; DMSO-d$_6$): δ 34.1, 68.2, 115.6, 120.5, 122.0, 125.8, 128.3, 130.0, 130.7, 132.0, 132.3, 134.6, 135.2, 137.8, 147.7, 160.2, 167.6, 168.1.

5-([4-[2-(4-(Benzenesulfonyloxy)phenyl)ethoxy]phenyl]methyl)thiazolidine-2,4-dione 1.5 g (3.1 mmole) 5-(4-[2-(4-(benzenesulfonyloxy)phenyl)ethoxy]benzylidene)thiazolidine-2,4-dione was hydrogenated on 1 g Pd/C (5%) in ethyl acetate and acetic acid (2.5%) at atmospheric pressure for 24 hours. The reaction mixture was filtered through celite and the solvent was evaporated in vacuo. The starting material was not completely consumed, therefore the hydrogenation was restarted twice with Pd/C (10%), followed by purification by chromatography on silica gel using dichloromethane:methanol (95:5) as eluent to give 0.728 g (yield 48.6%) of the desired product.

$^1$H-NMR (400 MHz; CDCl$_3$): δ 3.01–3.14 (m, 3H), 3.40–3.49 (dd, 1H), 4.09–4.15 (tr, 2H), 4.47–4.53 (dd, 1H), 6.78–6.86 (d, 2H), 6.89–6.96 (d, 2H), 7.10–7.16 (m, 2H), 7.17–7.23 (d, 2H), 7.49–7.57 (tr, 2H), 7.63–7.71 (tr, 1H), 7.81–7.88 (d, 2H). $^{13}$C-NMR (125 MHz; CDCl$_3$): δ 34.8, 37.5, 53.5, 68.0, 114.6, 122.0, 127.7, 128.2, 128.9, 129.9, 130.1, 134.0, 135.2, 137.3, 147.9, 157.9, 170.8, 174.5.

Example 17

2-[4-(Methylmercapto)phenyl]-1-ethanol 5.5 ml 1 M borane-tetrahydrofuiran complex was slowly added to a solution of 1 g (5.5 mmole) 4-(methylmercapto) phenyl acetic acid in 5 ml tetrahydrofuran at −10° C. The reaction mixture was allowed to reach room temperature and the reaction was followed by TLC. After completion 10 ml methanol was added and the solvents were evaporated. Diethyl ether and 2 M sodium hydroxide was added, the phases were separated, the organic phase was dried, filtered and evaporated in vacuo to give 0.8 g (yield 84.4%) of 2-[4-(methylmercapto)phenyl]-1-ethanol.

$^1$H-NMR (400 MHz; CDCl$_3$): δ 2.46 (s, 3H), 2.77–2.83 (tr, 2H), 3.74–3.82 (qvart, 2H), 7.12–7.17 (m, 2H), 7.20–7.24 (m, 2H). $^{13}$C-NMR (100 MHz; CDCl$_3$): δ 16.2, 38.6, 63.5, 127.2, 129.6, 137.7, 136.2.

4-[2-(4-Methylmercaptophenyl)ethoxy]benzaldehyde 1.7 g (10 mmole) 2-[4-(methylsulfanyl)phenyl]-1-ethanol, 5.24 g (20 mmole) triphenylphosphine and 5.05 g (20 mmole) 1,1-(azodicarbonyl)dipiperidine was added to a mixture of 2.47 g (20 mmole) 4-hydroxybenzaldehyde in 40 ml dichloromethane under argon atmosphere. Stirring at room temperature for 2 hours, (more dichloromethane was added after 20 minutes), gave a solid material that was removed by filtration. The filtrate was purified by chromatography on silica gel using dichloromethane as eluent to give 2.3 g (yield 84.4%) of 4-[2-(4-methylmercaptophenyl)ethoxy]benzaldehyde.

$^{13}$C-NMR (100 MHz; CDCl$_3$): δ 16.1, 35.1, 68.9, 114.8, 127.1, 129.5, 130.1, 132.0, 134.7, 136.7, 163.8, 190.7.

5-(4-[2-(4-Methylmercaptophenyl)ethoxy]benzylidene)thiazolidine-2,4-dione 1 g (3.7 mmole) 4-[2-(4-Methylmercaptophenyl)ethoxy]benzaldehyde, 1.09 (9.25 mmole) 2,4-thiazolidinedione, 5 drops of piperidine, 6 drops of acetic acid and toluene were refluxed with water separation in a Dean-Stark apparatus for 1 hour. The heat was removed and the crystals were recrystallized in dichloromethane:methanol (95:5) to give 1.1 g (yield 80%) of 5-(4-[2-(4-methylmercaptophenyl)ethoxy]benzylidene)thiazolidine-2,4-dione.

$^1$H-NMR (500 MHz; DMSO-d$_6$): δ 2.46 (s, 3H), 3.0–3.05 (tr, 2H), 4.22–4.38 (tr, 2H), 7.08–7.12 (m, 2H), 7.21–7.24 (m, 2H), 7.27–7.31 (m, 2H), 7.53–7.57 (m, 2H), 7.75 (s, 1H), 12.54 (bs, 1H). $^{13}$C-NMR (125 MHz; DMSO-d$_6$): δ 15.2, 34.4, 68.6, 115.6, 120.5, 125.7, 126.4, 129.8, 132.0, 132.3, 135.1, 136.0, 160.3, 167.7, 168.2.

5-([4-[2-(4-Methylmercaptophenyl)ethoxy]phenyl]methyl)thiazolidine-2,4-dione 1 g (2.7 mmole) 5-(4-[2-(4-methylmercaptophenyl)ethoxy]benzylidene)thiazolidine-2,4-dione and 1.36 g (5.4 mmole) diethyl-1,4-dihydro-2,6-dimethyl-3,5-pyridinedicarboxylate were mixed and heated to 160° C. under vacuum (when it melted), after 1 hour at this temperature the heat was removed. Toluene was added, crystals of the starting material was removed by filtration, the filtrate was evaporated and purified by chromatography on silica gel twice using first dichloromethane:methanol (98:2) and then diisopropyl ether as eluents. The reaction was restarted with unreacted material and 0.4 g diethyl-1,4-dihydro-2,6-dimethyl-3,5-pyridinedicarboxylate and kept at 160° C. for 2 hours. The product was boiled in diisopropyl ether, and purified by chromatography on silica gel using diisopropyl ether as eluent. The combined fractions gave 0.346 g (yield 36%) of the desired product.

$^1$H-NMR (500 MHz; CDCl$_3$): δ 2.53 (s, 3H), 3.08–3.18 (m, 3H), 3.46–3.54 (dd, 1H), 4.16–4.22 (tr, 2H), 4.52–4.58 (dd, 1H), 6.87–6.92 (m, 2H), 7.16–7.20 (m, 2H), 7.25–7.30 (m, 4H). $^{13}$C-NMR (125 MHz; CDCl$_3$): δ 15.9, 35.0, 37.5, 53.5, 68.4, 114.6, 126.8, 129.3, 130.1, 127.5, 135.1, 136.2, 158.1, 170.3, 174.4.

Example 18

2-[4-(Methylsulfonyl)phenyl]-1-ethanol 10 g (47 mmole) 4-(methylsulfonyl)phenyl acetic acid was dissolved in 40 ml tetrahydrofuran and the solution was cooled to −10° C. At this temperature 4-(methylsulfonyl) phenyl acetic acid precipitates. 47 ml 1 M borane-tetrahydrofuran complex was added slowly. The reaction mixture was allowed to reach room temperature and the reaction was followed by TLC. After completion 100 ml methanol was added and the solvents were evaporated. The residue was dissolved in dichloromethane and washed with sodium hydroxide. The organic phase was dried, filtered and evaporated in vacuo to give 7.5 g (yield 79.7%) of 2-[4-(methylsulfonyl)phenyl]-1-ethanol.

$^1$H-NMR (400 MHz; CDCl$_3$): δ 1.73 (m, 1H), δ 2.96 (tr, 2H), 3.05 (s, 3H), 3.91 (q, 2H), 7.45 (m, 2H), 7.87 (m, 2H).

4-[2-(4-Formylphenoxy)ethyl]phenyl methyl sulfone 1.83 g (15 mmole) 4-hydroxybenzaldehyde was dissolved in 35 ml dichloromethane under argon atmosphere. 1.5 g (7.5 mmole) 2-[4-(methylsulfonyl)phenyl]-1-ethanol was added followed by 3.93 g (15 mmole) triphenylphosphine and 3.78 g (15 mmole) 1,1-(azodicarbonyl)dipiperidine. The reaction mixture was stirred at room temperature and after 2 hours a precipitate is observed. The reaction was disrupted after 5 hours and the reaction mixture was filtered. The filtrate was purified by chromatography on silica gel using dichloromethane:methanol (98:2) as eluent giving 1.66 g (yield 54.5%) of 4-[2-(4-formylphenoxy)ethyl]phenyl methyl sulfone.

$^1$H-NMR (400 MHz; CDCl$_3$): δ 3.04 (s,3H), 3.22 (tr, 2H), 4.30 (tr, 2H), 6.96–7.00 (m, 2H), 7.48–7.52(m, 42H), 7.80–7.85 (m, 2H), 7.88–7.91(m, 2H), 9.87 (s, 1H).

5-(4-[2-(4-Methanesulfonylphenyl)ethoxy]benzylidene)thiazolidine-2,4-dione 1 g (3.3 mmole) 4-[2-(4-formylphenoxy)ethyl]phenyl methyl sulfone, 0.96 g (8.2 mmole) 2,4-thiazolidinedione, 5 drops of piperidine, 6 drops of acetic acid and toluene were refluxed with water separation in a Dean-Stark apparatus for 1 hour. The heat was removed and the yellow precipitate was filtered off. A slurry of the precipitate and dichloromethane:methanol (95:5) was refluxed. The product was collected by filtration giving 0.9 g (yield 67.6%) of 5-(4-[2-(4-methanesulfonylphenyl)ethoxy]benzylidene) thiazolidine-2,4-dione.

$^1$H-NMR (500 MHz; DMSO-d$_6$): δ 3.13–3.18 (m, 5H), 4.31 (tr, 2H), 7.06–7.10 (m, 2H), 7.50–7.54 (m, 2H), 7.72 (s, 1H), 7.57–7.61 (m, 2H), 7.82–7.87 (m, 2H), 12.50 (bs, 1H). $^{13}$C-NMR (125 MHz; DMSO-d$_6$): δ 35.0, 44.1, 68.2, 115.9, 121.0, 126.2, 127.4, 130.4, 132.1, 132.5, 139.5, 145.0, 160.5, 168.0, 168.4.

5-([4-[2-(4-Methanesulfonylphenyl)ethoxy]phenyl]methyl)thiazolidine-2,4-dione 0.9 g (2.2 mmole) 5-(4-[2-(4-methanesulfonylphenyl) ethoxy]benzylidene)thiazolidine-2,4-dione was dissolved in approximately 550 ml ethyl acetate/acetic acid (0.9%) under heating. Pd/C (10%) was added as catalyst to the warm solution followed by hydrogenation for 17 hours. The reaction mixture was filtered through celite and the solvent was evaporated in vacuo.

The yellow residue was refluxed in dichloromethane. The solid material was filtered off and purified by flash chromatography using dichloromethane:methanol (95:5) The product still contained some unreacted starting material and it was therefore hydrogenated once more with Pd/C (10%) in ethyl acetate. Filtration through celite gave 0.25 g (yield 28%) of the desired product.

$^1$H-NMR (500 MHz; CDCl$_3$): δ 3.0–3.1 (m, 6H), 3.15 (tr, 2H), 4.35–4.45 (dd, 1H), 4.2 (tr, 2H), 4.42–4.5 (dd, 1H), 6.8 (d, 2H), 7.15 (d, 2H), 7.5 (d, 4H), 7.85 (d, 2H). $^{13}$C-NMR (125 MHz; CDCl$_3$): δ 35.6, 37.6, 44.5, 53.7, 67.7, 114.8, 127.5, 128.1, 130.0, 130.4, 138.6, 135.1, 157.9, 170.9, 174.7.

Example 19

3-Methoxy-4-(methylsulfonyloxy)phenethyl methanesulfonate 44 g (0.39 mole) methanesulfonyl chloride was slowly added to a solution of 30 g (0.178 mole) homovanillyl alcohol and 45.3 g (0.45 mmole) triethylamine in 500 ml dichloromethane at −10° C. After stirring at room temperature over night the salts were filtered off, the organic phase was washed with sodium bicarbonate and brine, dried (magnesium sulfate) and evaporated in vacuo to give 50 g (yield 86%) of 3-methoxy-4-(methylsulfonyloxy)phenethyl methanesulfonate.

4-[2-(4-Formylphenoxy)ethyl]-2-methoxyphenyl methanesulfonate 50 g (0.154 mole) 3-methoxy-4-(methylsulfonyloxy) phenethyl methanesulfonate, 48.8 g 0.4 mole) p-hydroxybenzaldehyde, 65.45 g 0.473 mole) potassium carbonate in 500 ml acetonitrile was refluxed for 4 hours. The precipitate was filtered off and the solvent was evaporated. Dichloromethane was added and the organic phase was washed with water, dried (magnesium sulfate), filtered and the solvent was evaporated to give 34 g (yield 63%) of 4-[2-(4-formylphenoxy)ethyl]-2-methoxyphenyl methanesulfonate.

5-(4-[2-(3-Methoxy-4-methanesulfonyloxyphenyl)ethoxy]benzylidene)thiazolidine-2,4-dione 34 g (97 mmole) 4-[2-(4-formylphenoxy)ethyl]-2-methoxyphenyl methanesulfonate, 12.5 g (107 mmole) 2,4-thiazolidinedione, 0.5 ml piperidine and 0.5 ml acetic acid in 500 ml toluene was refluxed with water separation in a Dean-Stark apparatus for 4 hours. The solvent was evaporated, acetic acid was added and the mixture was heated. The formed precipitate was filtered and washed with diethyl ether to give 31.5 g (yield 72%) of 5-(4-[2-(3-methoxy-4-methanesulfonyloxyphenyl)ethoxy] benzylidene)thiazolidine-2,4-dione.

¹H-NMR (300 MHz; DMSO-d₆): δ 3.0–3.12 (t, 2H), 3.3 (s, 3H), 3.85 (s, 3H), 4.22–4.35 (t, 2H), 6.9–7.0 (d, 1H), 7.05–7.15 (m, 2H), 7.15–7.27 (d, 2H), 7.5–7.6 (d, 2H), 7.75 (s, 1H).

5-([4-[2-(3-Methoxy-4-methanesulfonyloxyphenyl)ethoxy]phenyl]methyl)thiazolidine-2,4-dione 1.5 g (33.4 mmole) 5-(4-[2-(3-methoxy-4-methanesulfonyloxyphenyl)ethoxy]benzylidene)thiazolidine-2,4-dione was hydrogenated on Pd/C (10%) in 150 ml ethyl acetate and 5 ml acetic acid at atmospheric pressure over night. The catalyst was filtered off and the solvent was evaporated in vacuo. The residue was crystallized in ethanol to give 1.1 g (yield 73%) of the desired product.

¹H-NMR (300 MHz; DMSO-d₆): δ 2.97–3.15 (m, 3H), 3.25–3.4 (m and s, 4H), 3.85 (s, 3H), 4.15–4.25 (m, 2H), 4.77–4.9 (m, 1H), 6.82–7.0 (m, 3H), 7.1–7.3 (m, 4H) ¹³C-NMR (75 MHz; DMSO-d₆): δ 34.7, 36.2, 38.1, 53.0, 55.7, 67.6, 114.1, 114.2, 121.0, 123.5, 128.6, 130.3, 136.3, 138.9, 151.0, 157.3, 171.7, 175.8.

Example 20

3-(Methylsulfonyloxy)phenethyl methanesulfonate 9.09 g (79.6 mmole) methanesulfonyl chloride was slowly added to a solution of 5 g (36.2 mmole) 3-hydroxyphenethyl alcohol and 9.14 g (90.5 mmole) triethylamine in 150 ml dichloromethane at 0° C. After stirring at room temperature over night the salts were filtered off, the organic phase was washed with sodium bicarbonate and brine, dried (magnesium sulfate) and evaporated in vacuo to give 9.3 g (yield 87%) of 3-(methylsulfonyloxy)phenethyl methanesulfonate.

3-[2-(4-Formylphenoxy)ethyl]phenyl methanesulfonate 9.3 g (31.6 mmole) 3-(methylsulfonyloxy)phenethyl methanesulfonate, 9.91 g (82 mmole) p-hydroxybenzaldehyde and 13 g (94.8 mmole) potassium carbonate in 200 ml acetonitrile were refluxed for 4 hours. The precipitate was filtered off and the solvent was evaporated in vacuo. Dichloromethane was added and the organic phase was washed with water, dried (magnesium sulfate), filtered and the solvent was evaporated to give 8.72 g (yield 88%) of 3-[2-(4-formylphenoxy)ethyl]phenyl methanesulfonate.

5-(4-[2-(3-Methanesulfonyloxyphenyl)ethoxy]benzylidene)thiazolidine-2,4-dione 5.31 g (16.6 mmole) 3-[2-(4-formylphenoxy)ethyl]phenyl methanesulfonate, 2.13 g (18.2 mmole) 2,4-thiazolidinedione, 0.5 ml piperidine and 0.5 ml acetic acid in 300 ml toluene were refluxed with water separation in a Dean-Stark apparatus for 4 hours. The solvent was evaporated, acetic acid was added and the mixture was heated. The formed precipitate was filtered off and washed with diethyl ether to give 3.6 g (yield 51%) of 5-(4-[2-(3-methanesulfonyloxyphenyl)ethoxy]benzylidene)thiazolidine-2,4-dione.

¹H-NMR (300 MHz; DMSO-d₆): δ 3.05–3.17 (tr, 2H), 3.37 (s, 3H), 4.25–4.35 (tr, 2H), 7.05–7.13 (d, 2H), 7.17–7.26 (d, 1H), 7.3–7.4 (m, 2H), 7.4–7.48 (m, 1H). 7.49–7.59 (d, 2H), 7.75 (s, 1H). ¹³C-NMR (75 MHz; DMSO-d₆): δ 34.2, 37.3, 67.9, 115.3, 120.1, 120.2, 122.6, 125.5, 127.9, 129.8, 131.7, 132.0, 140.7, 149.0, 166.0, 167.3, 167.8.

5-([4-[2-(3-Methanesulfonyloxyphenyl)ethoxy]phenyl]methyl)thiazolidine-2,4-dione 2 g (84 mmole) 5-(4-[2-(3-methanesulfonyloxyphenyl)ethoxy]benzylidene)thiazolidine-2,4-dione was hydrogenated in 200 ml ethyl acetate and 10 ml acetic acid in the presence of Pd/C (10%) at atmospheric pressure over night. The catalyst was filtered off and the solvent was evaporated in vacuo. The residue was crystallized in ethanol to give 1.18 g (yield 59%) of the desired product.

¹H-NMR (300 MHz; DMSO-d₆): δ 3.0–3.15 (m, 3H), 3.25–3.45 (m, 4H); 4.1–4.25 (d, 2H), 4.8–4.9 (m, 1H), 6.8–6.95 (d, 2H), 7.1–7.2 (d, 2H), 7.2–7.3 (d, 1H), 7.3–7.5 (m, 3H). ¹³C-NMR (75 MHz; DMSO-d₆): δ 34.4, 36.2, 37.2, 53.0, 67.5, 114.3, 120.0, 122.6, 127.9, 128.6, 129.8, 130.3, 141.0, 149.0, 157.3, 171.8, 175.8.

Example 21

4-(Trifluoromethylsulfonyloxy)phenethyl trifluoromethansulfonate 10.3 g (75 nmuole) p-hydroxyphenethyl alcohol was dissolved in dichloromethane. 37 g (0.18 mole) 2,6-di-tertbutyl-4-metylpyridine was added followed by slow addition of a solution of 48.5 g (0.172 mole) trifluoroacetic anhydride in dichloromethane at 0° C. The reaction was allowed to reach room temperature and stirred for 48 hours. The reaction mixture was filtered and the filtrate was evaporated in vacuo. The residue was purified by chromatography on silica gel using dichloromethane as eluent to give 20 g (yield 76.2%) of 4-(trifluoromethylsulfonyloxy)phenethyl trifluoromethansulfonate.

4-[2-(4-Formylphenoxy)ethyl]phenyl trifluoromethanesulfonate

A mixture of 0.85 g (2.11 mmole) of 4-(trifluoromethylsulfonyloxy)phenethyl trifluoromethansulfonate, 0.27 g (2.2 mmole) p-hydroxybenzaldehyde and 0.72 g (2.2 mmole) cesium carbonate in acetonitrile was stirred at room temperature over night. The salts were filtered off and the solvent evaporated in vacuo. Purification by chromatography on silica gel using dichloromethane as eluent gave 0.6 g (yield 75%) of 4-[2-(4-formylphenoxy)ethyl]phenyl trifluoromethanesulfonate.

5-(4-[2-(4-Trifluoromethanesulfonyloxyphenyl)ethoxy]benzylidene)thiazolidine-2,4-dione 7 g (18.7 mmole) of 4-[2-(4-formylphenoxy)ethyl]phenyl trifluoromethanesulfonate, 2.74 g (23.4 mmole) 2,4-thiazolidinedione and 3.8 g (46.8 mmole) sodium acetate were mixed and heated under vacuum to 140° C. when it melted. It was kept at 140° C. for 20 minutes and thereafter taken off the heat, water:acetone (2:1) was added, the formed crystals were filtered off and recrystallization in dichloromethane gave 2.09 g (yield 24%) 5-(4-[2-(4-trifluoromethanesulfonyloxyphenyl)ethoxy]benzylidene)thiazolidine-2,4-dione.

¹H-NMR (300 MHz; DMSO-d₆): δ 3.02–3.12 (tr, 2H), 4.2–4.35 (tr, 2H), 7.0–7.1 (m, 2H), 7.35–7.45 (m, 2H), 7.45–7.56 (m, 4H), 7.75 (s, 1H). ¹³C-NMR (75 MHz; DMSO-d₆): δ 34.2, 68.1, 115.6, 120.5, 121.4, 125.8, 128(q, J=8), 131.4, 132.0, 132.3, 139.6, 148.1, 160.2, 167.6, 168.2.

5-([4-[2-(4-Trifluoromethanesulfonyloxyphenyl)ethoxy]phenyl]methyl)thiazolidine-2,4-dione 2 g (4.22 mmole) 5-(4-[2-(4-trifluoromethanesulfonyloxyphenyl)ethoxy]benzylidene)

thiazolidine-2,4-dione and 2.14 g (8.44 mmole) diethyl-1,4-dihydro-2,6-dimethyl-3.5-pyridine dicarboxylate were mixed and heated to 180° C. under vacuum when it melted, the temperature raised to 230° C. and after 30 minutes the heat was removed. Purification by chromatography on silica gel with heptane/ethyl acetate as eluent gave 0.768 g (yield 38%) of the desired product.

$^1$H-NMR (300 MHz; DMSO-d$_6$): δ 2.95–3.45 (m, 3H), 4.05–4.25 (m, 2H), 4.8–4.9 (m, 1H), 6.8–6.95 (m, 2H), 7.05–7.20 (m, 2H), 7.35–7.47 (m, 2H), 7.47–7.6 (m, 2H).

Biological Activity

The biological activity of the compounds was tested in obese diabetic mice of the Umeå ob/ob strain. Groups of mice received the test compound by gavage once daily for 7 days. On the last day of the experiment the animals were anesthetized 2 h after dose in a non-fed state and blood was collected from an incised artery. Plasma was analyzed for concentration of glucose, insulin and triglycerides. A group of untreated obese diabetic mice of the same age served as control. The individual values for glucose, insulin and triglyceride levels of the mice from the test group were expressed as the percent rage of the corresponding values from the control group.

The desired "therapeutic effect" was calculated as the average percent reduction of the three variables glucose, insulin and triglycerides below the levels in the control animals. The therapeutic effect of the tested compounds according to the invention was compared to the same effect in the prior art compound troglitazone, administrered by gavage in the oral dose of 300 μmol/kg for 7 days.

The superior effects of the tested compounds according to the invention compared to that of troglitazone when given in the same oral dose demonstrate the increased potency and efficacy of the claimed compounds.

What is claimed is:

1. A compound of formula I

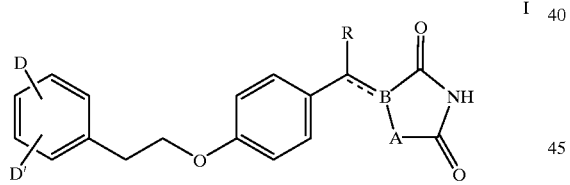

I or a stereo- or optical isomer or racemate thereof, in which formula ≡ is a single or double bond,
R is H or alkyl,
A is S, O or NH,
B is C, CH or N,
D is CN or —X—Y—Z and is situated in the ortho, meta or para position,
D' is H, —O-alkyl, alkyl, halogen or —X—Y—Z and is situated in the ortho, meta or para position, wherein
X is O, NR$^1$, SO$_2$ or S and R$^1$ is H or alkyl,
Y is SO$_2$, CO or a chemical bond,
Z is alkyl, alkyl substituted by one or more fluoro or chloro atoms, aryl, substituted aryl, alkylaryl, OR$^2$ or NHR$^3$, wherein
R$^2$ is alkyl, aryl, alkylaryl, substituted aryl or substituted alkyl, and
R$^3$ is H, alkyl, aryl, alkylaryl, substituted aryl or substituted alkyl, provided that
when X is O or NR$^1$, then Y is either SO$_2$ or CO, and
a) when X is O or NR$^1$, and Y is SO$_2$, Z is selected from the group consisting of alkyl, alkyl substituted by one or more fluoro or chloro atoms, aryl, substituted aryl and alkylaryl,
b) when X is O or NR$^1$, and Y is CO, Z is selected from the group consisting of OR$^2$ and NHR$^3$;
when X is SO$_2$, then Y is a chemical bond and Z is selected from the group consisting of alkyl, alkyl substituted by one or more fluoro or chloro atoms, aryl, substituted aryl, alkylaryl and OR$^2$;
when X is S, then Y is a chemical bond and Z is selected from the group consisting of alkyl, alkyl substituted by one or more fluoro or chloro atoms, aryl, substituted aryl and alkylaryl;
and further provided that when B is N, A is O,
and wherein the compound, isomer, or racemate thereof may exist in the form of a pharmaceutically acceptable salt, solvate, and/or hydrate thereof.

2. A compound according to claim 1, wherein ≡ is a single or double bond,
R is H or alkyl,
A is S or O,
B is C, CH or N,
D is —X—Y—Z and is situated in the ortho, meta or para position,
D' is H, —O-alkyl or —X—Y—Z and is situated in the ortho, meta or para position, wherein
X is O, NR$^1$, SO$_2$, or S wherein R$^1$ is H or alkyl,
Y is SO$_2$, CO or a chemical bond,
Z is alkyl, aryl, alkylaryl, substituted aryl, CF$_3$, OR$^2$ or NHR$^3$, wherein R$^2$ and R$^3$ are as defined in claim 1,
provided that
when X is O or NR$^1$ then Y is either SO$_2$ or CO, and
a) when X is O or NR$^1$, and Y is SO$_2$, Z is selected from the group consisting of alkyl, CF$_3$, aryl, substituted aryl and alkylaryl,
b) when X is O or NR$^1$, and Y is CO, Z is selected from the group consisting of OR$^2$ and NHR$^3$;
when X is SO$_2$, then Y is a chemical bond and Z is selected from the group consisting of alkyl, CF$_3$, aryl, substituted aryl, alkylaryl and OR$^2$;
when X is S, then Y is a chemical bond and Z is selected from the group consisting of alkyl, CF$_3$, aryl, substituted aryl and alkylaryl;
and further provided that when B is N, A is O.

3. A compound according to claim 1 or 2 wherein ≡ is a single or double bond,
R is H,
A is S,
B is C or CH,
D is —X—Y—Z and is situated in the ortho, meta or para position,
D' is H,
X is O, NR$^1$, SO$_2$, or S wherein R$^1$ is H or alkyl,
Y is SO$_2$, CO or a chemical bond,
Z is alkyl, aryl, alkylaryl, substituted aryl, CF$_3$, OR$^2$ or NHR$^3$, wherein R$^2$ and R$^3$ are as defined in claim 1,
provided that
when X is C or NR$^1$, then Y is either SO$_2$ or CO, and
a) when X is O or NR$^1$, and Y is SO$_2$, Z is selected from the group consisting of alkyl, CF$_3$, aryl, substituted aryl and alkylaryl,
b) when X is O or NR$^1$, and Y is CO, Z is selected from the group consisting of OR$^2$ and NHR$^3$;

when X is SO₂, then Y is a chemical bond and Z is selected from the group consisting of alkyl, CF₃, aryl, substituted aryl, alkylaryl and OR²;

when X is S, then Y is a chemical bond and Z is selected from the group consisting of alkyl, CF₃, aryl, substituted aryl and alkylaryl.

4. A compound according to claim 1 or 2 wherein ≡ is a single bond or double bond, R is H, A is S, B is C or CH, D is —X—Y—Z and is situated in the ortho, meta or para position, D' is H, X is O, NH, SO₂ or S, Y is SO₂, CO or a chemical bond, Z is alkyl, aryl, alkylaryl, substituted aryl, CF₃, OR² or NHR³, wherein R² and R³ are as defined in claim 1, provided that when X is O or NH, then Y is either SO₂ or CO, and
  a) when X is O or NH, and Y is SO₂, Z is selected from the group consisting of alkyl, CF₃, aryl, substituted aryl and alkylaryl,
  b) when X is O or NH and Y is CO, Z is selected from the group consisting of OR² and NHR³;

when X is SO₂, then Y is a chemical bond and Z is selected from the group consisting of alkyl, CF₃, aryl, substituted aryl, alkylaryl and OR²;

when X is S, then Y is a chemical bond and Z is selected from the group consisting of alkyl, CF₃, aryl, substituted aryl and alkylaryl.

5. A compound according to claim 1 or 2 wherein D is situated in the para position.

6. A compound according to claim 1 or 2 wherein ≡ is a single bond,

R is H,

A is S,

B is CH,

D is —X—Y—Z and is situated in the para position,

D' is H,

X is O or NH,

Y is SO₂ or CO,

Z is selected from the group consisting of alkyl, aryl, alkylaryl, substituted aryl, CF₃, OR² and NHR³, wherein R² and R³ are as defined in claim 1, provided that when X is O or NH, then Y is either SO₂ or CO, and
  a) when X is O or NH, and Y is SO₂, Z is selected from the group consisting of alkyl, CF₃, aryl, substituted aryl and alkylaryl,
  b) when X is O or NH, and Y is CO, Z is selected from the group consisting of OR² and NHR³.

7. A compound according to claim 1 or 2 wherein ≡ is a single bond,

R is H,

A is S,

B is CH,

D is —X—Y—Z and is situated in the para position,

D' is H,

X is O or NH,

Y is SO₂ or CO,

Z is alkyl, NHR³ or OR², wherein R² is alkyl and R³ is alkyl, provided that when X is O or NH, then Y is either SO₂ or CO, and
  a) when X is O or NH, and Y is SO₂, Z is alkyl,
  b) when X is O or NH and Y is CO, Z is selected from the group consisting of OR² and NHR³.

8. A compound according to claim 1 or 2 of the formula

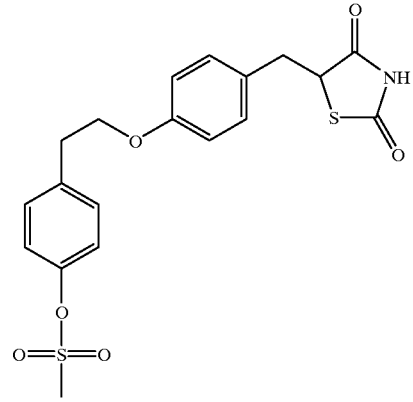

or

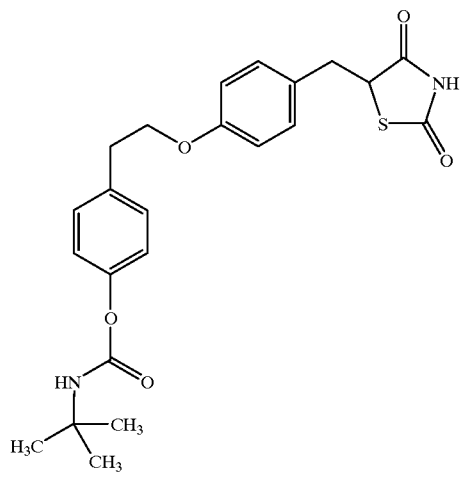

or

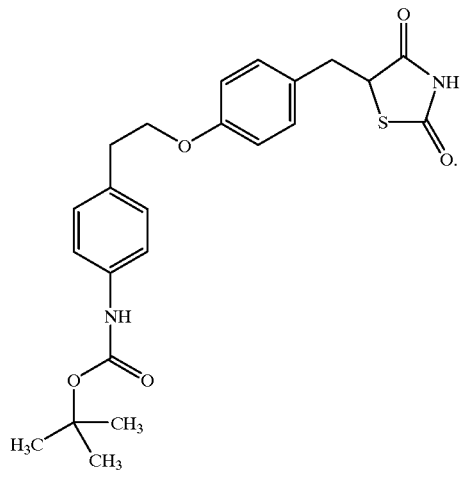

9. A process for preparing a compound according to claim 1, the process comprising a) condensing a carbonyl compound of formula II

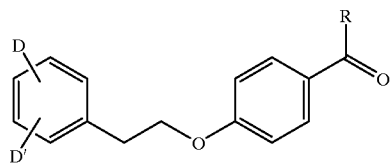

with a compound of the formula

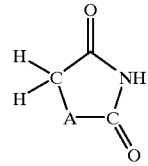

optionally followed by reduction of the obtained compound, to form a compound of formula I of claim 1, wherein D, D', and R are as defined in claim 1, and A is S or O, and B is C or CH; or b) reacting a compound of the formula
with a compound of the formula

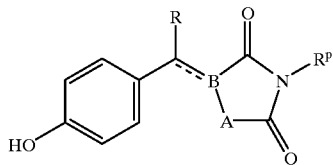

wherein D, D', R, A and B are as defined in claim 1, $R^x$ is a leaving group or a hydroxyl group and $R^p$ is

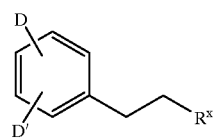

hydrogen or a protecting group, followed if necessary by removal of the protecting group, to form a compound of formula I of claim 1; or c) reacting a compound of the formula

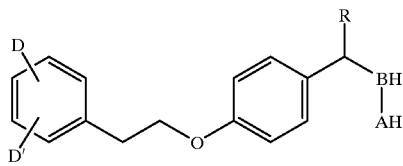

with a compound of the formula

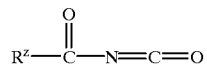

wherein D, D', and R are as defined in claim 1, A is O, B is N, and $R^z$ is a halogen, to form a compound of formula I of claim 1 wherein A is O, B is N and ==== is a single bond, whereafter, if desired, the compound obtained according to any of processes a)–c) is converted to a stereoisomer and/or a pharmaceutically acceptable salt thereof.

10. A pharmaceutical formulation containing a compound according to claim 1 or 2 as active ingredient optionally together with an acceptable carrier.

11. A method for the treatment of clinical conditions associated with insulin resistance which comprises administration of a therapeutically active amount of a compound according to claim 1 or 2 to a mammal in need of such treatment.

* * * * *

UNITED STATES PATENT AND TRADEMARK OFFICE
CERTIFICATE OF CORRECTION

PATENT NO. : 6,288,096 B1
DATED : September 11, 2001
INVENTOR(S) : Andersson et al.

It is certified that error appears in the above-identified patent and that said Letters Patent is hereby corrected as shown below:

Column 3,
Line 54, " ═ " and substitute therefor " --- ";

Column 4,
Line 26, " ═ " and substitute therefor " --- ";
Line 56, " ═ " and substitute therefor " --- ";

Column 5,
Line 16, " ═ " and substitute therefor " --- ";
Line 47, " ═ " and substitute therefor " --- ";
Line 67, " ═ " and substitute therefor " --- ";

Column 8,
Line 66, " ═ " and substitute therefor " --- ";

Column 9,
Line 11, " ═ " and substitute therefor " --- ";

Column 10,
Line 33, " ═ " and substitute therefor " --- ";

Column 35, claim 1,
Line 50, " ═ " and substitute therefor " --- ";

UNITED STATES PATENT AND TRADEMARK OFFICE
CERTIFICATE OF CORRECTION

PATENT NO. : 6,288,096 B1
DATED : September 11, 2001
INVENTOR(S) : Andersson et al.

It is certified that error appears in the above-identified patent and that said Letters Patent is hereby corrected as shown below:

Column 36, claim 2,
Line 20, "≡" and substitute therefor "---":

Column 36, claim 3,
Line 48, "≡" and substitute therefor "---":

Column 37, claim 4,
Line 7, "≡" and substitute therefor "---":

Column 37, claim 5,
Line 37, "≡" and substitute therefor "---":

Column 37, claim 6,
Line 58, "≡" and substitute therefor "---":

Column 40, claim 9,
Line 30, "≡" and substitute therefor "---":

Column 36, claim 3,
Line 62, delete "X is C or NR$^1$" and substitute therefor
-- X is O or NR$^1$. --

UNITED STATES PATENT AND TRADEMARK OFFICE
CERTIFICATE OF CORRECTION

PATENT NO.    : 6,288,096 B1
DATED         : September 11, 2001
INVENTOR(S)   : Andersson et al.

It is certified that error appears in the above-identified patent and that said Letters Patent is hereby corrected as shown below:

Claim 9,
Delete the text between col. 39, line 26 and col. 40, line 3, and substitute therefor:

b) reacting a compound of the formula

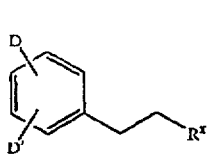

III with a compound of the formula

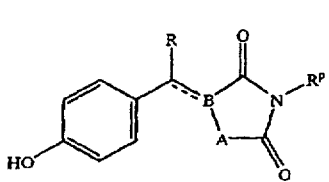

IV wherein D, D', R, A and B are as defined in claim 1, $R^x$ is a leaving group or a hydroxyl group and $R^p$ is hydrogen or a protecting group, followed if necessary by removal of the protecting group, to form a compound of formula I of claim 1; or Signed and Sealed this Twenty-third Day of April, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO.   : 6,288,096 B1
DATED        : September 11, 2001
INVENTOR(S)  : Andersson et al.

It is certified that error appears in the above-identified patent and that said Letters Patent is hereby corrected as shown below:

Column 3,
Line 54, delete " = " and substitute therefor " --- ";

Column 4,
Line 26, delete " = " and substitute therefor " --- ";

Line 56, delete " = " and substitute therefor " --- ";

Column 5,
Line 16, delete " = " and substitute therefor " --- ";

Line 47, delete " = " and substitute therefor " --- ";

Line 67, delete " = " and substitute therefor " --- ";

Column 8,
Line 66, delete " = " and substitute therefor " --- ";

Column 9,
Line 11, delete " = " and substitute therefor " --- ";

Column 10,
Line 33, delete " = " and substitute therefor " --- ";

Column 35, claim 1,
Line 50, delete " = " and substitute therefor " --- ";

UNITED STATES PATENT AND TRADEMARK OFFICE
CERTIFICATE OF CORRECTION

PATENT NO. : 6,288,096 B1
DATED : September 11, 2001
INVENTOR(S) : Andersson et al.

It is certified that error appears in the above-identified patent and that said Letters Patent is hereby corrected as shown below:

Column 36, claim 2,
Line 20, delete " ═ " and substitute therefor " --- ";

Column 36, claim 3,
Line 48, delete " ═ " and substitute therefor " --- ";

Column 37, claim 4,
Line 7, delete " ═ " and substitute therefor " --- ";

Column 37, claim 5,
Line 37, delete " ═ " and substitute therefor " --- ";

Column 37, claim 6,
Line 58, delete " ═ " and substitute therefor " --- ";

Column 40, claim 9,
Line 30, delete " ═ " and substitute therefor " --- ";

Column 36, claim 3,
Line 62, delete "X is C or $NR^1$" and substitute therefor
-- X is O or $NR^1$. --

UNITED STATES PATENT AND TRADEMARK OFFICE
CERTIFICATE OF CORRECTION

PATENT NO.    : 6,288,096 B1
DATED         : September 11, 2001
INVENTOR(S)   : Andersson et al.

It is certified that error appears in the above-identified patent and that said Letters Patent is hereby corrected as shown below:

<u>Claim 9,</u>
Delete the text between col. 39, line 26 and col. 40, line 3, and substitute therefor:

b) reacting a compound of the formula

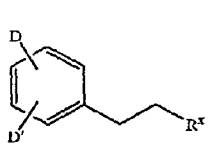

III with a compound of the formula

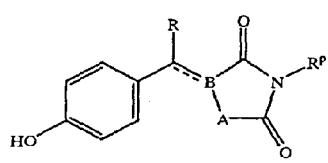

IV wherein D, D', R, A and B are as defined in claim 1, $R^x$ is a leaving group or a hydroxyl group and $R^p$ is hydrogen or a protecting group, followed if necessary by removal of the protecting group, to form a compound of formula I of claim 1; or This certificate supersedes Certificate of Correction issued April 23, 2002.

Signed and Sealed this

Twentieth Day of August, 2002

*Attest:*

*Attesting Officer*

JAMES E. ROGAN
*Director of the United States Patent and Trademark Office*